(12) United States Patent
Wilkinson et al.

(10) Patent No.: US 10,067,040 B2
(45) Date of Patent: Sep. 4, 2018

(54) MULTI-CHAMBERED TISSUE CONTAINMENT SYSTEM FOR MOLECULAR AND HISTOLOGY DIAGNOSTICS

(71) Applicant: Becton, Dickinson and Company, Franklin Lakes, NJ (US)

(72) Inventors: Bradley M. Wilkinson, North Haledon, NJ (US); C. Mark Newby, Tuxedo, NY (US); Clinton A. Haynes, Mason, OH (US); Robert G. States, III, Morrow, OH (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 474 days.

(21) Appl. No.: 14/309,123

(22) Filed: Jun. 19, 2014

(65) Prior Publication Data
US 2014/0302552 A1    Oct. 9, 2014

Related U.S. Application Data

(60) Division of application No. 13/864,447, filed on Apr. 17, 2013, now Pat. No. 8,802,038, which is a
(Continued)

(51) Int. Cl.
    *G01N 1/30*      (2006.01)
    *G01N 1/31*      (2006.01)
    (Continued)

(52) U.S. Cl.
    CPC ............... *G01N 1/30* (2013.01); *B01L 3/502* (2013.01); *B23P 17/00* (2013.01); *G01N 1/31* (2013.01);
(Continued)

(58) Field of Classification Search
CPC .... F16B 2/20; F16B 2/205; F16B 2/22; F16B 2/24; B01L 3/50825; B01L 2300/046; B01L 2300/0609
(Continued)

(56) References Cited

U.S. PATENT DOCUMENTS 3,918,920 A    11/1975   Barber
3,977,794 A    8/1976   Liedholz
(Continued)

FOREIGN PATENT DOCUMENTS

CN      1501080 A    6/2004
DE      20201894 U1    5/2002
(Continued)

*Primary Examiner* — Christopher Hixson
(74) *Attorney, Agent, or Firm* — The Webb Law Firm

(57) ABSTRACT

A container for storing a biological sample is disclosed. The container includes a first chamber having a sidewall extending between an open end and a closed end, defining a first chamber interior adapted to receive a sample holder therein. The container also includes a second chamber having a sidewall extending between an open end and a closed end, defining a second chamber interior adapted to subsequently receive the sample holder therein. The second chamber interior is in fluid isolation from the first chamber interior. A removable closure encloses at least one of the open end of the first chamber and the open end of the second chamber while the sample holder is disposed within one of the first chamber interior and the second chamber interior. A first fluid may be disposed within the first chamber interior, and a second different fluid may be disposed within the second chamber interior.

4 Claims, 21 Drawing Sheets

Related U.S. Application Data continuation of application No. 12/257,119, filed on Oct. 23, 2008, now Pat. No. 8,449,844.

(60) Provisional application No. 60/982,062, filed on Oct. 23, 2007.

(51) Int. Cl.
*B01L 3/00* (2006.01)
*G01N 1/36* (2006.01)
*B23P 17/00* (2006.01)

(52) U.S. Cl.
CPC ............ *G01N 1/36* (2013.01); *B01L 2300/02* (2013.01); *B01L 2300/044* (2013.01); *B01L 2300/046* (2013.01); *B01L 2300/0609* (2013.01); *B01L 2300/0858* (2013.01); *Y10T 29/49826* (2015.01); *Y10T 29/53443* (2015.01)

(58) Field of Classification Search
USPC .................................................... 248/346.03
See application file for complete search history.

(56) References Cited

U.S. PATENT DOCUMENTS

| | | | |
|---|---|---|---|
| 4,034,884 A | 7/1977 | White | |
| 4,076,592 A | 2/1978 | Bradley | |
| 4,094,483 A * | 6/1978 | Busch ................... | F16B 5/0685 248/222.12 |
| 4,220,252 A | 9/1980 | Beall et al. | |
| 4,416,984 A | 11/1983 | Wheeler, Jr. | |
| 4,675,299 A | 6/1987 | Witty et al. | |
| 4,903,869 A | 2/1990 | McKenna | |
| 5,098,663 A | 3/1992 | Berthold et al. | |
| 5,455,180 A | 10/1995 | Reid | |
| 5,665,398 A | 9/1997 | McCormick | |
| 5,743,861 A | 4/1998 | Columbus et al. | |
| 6,156,275 A | 12/2000 | Dumitrescu et al. | |
| 6,207,408 B1 | 3/2001 | Essenfeld et al. | |
| 7,147,826 B2 | 12/2006 | Haywood et al. | |
| 9,234,823 B2 | 1/2016 | Vom et al. | |
| 2002/0048819 A1 | 4/2002 | Alley | |
| 2003/0086830 A1 | 5/2003 | Haywood et al. | |
| 2004/0106097 A1 | 6/2004 | Hutter et al. | |
| 2004/0184954 A1 | 9/2004 | Guo et al. | |
| 2005/0163660 A1 | 7/2005 | Wang | |
| 2006/0154281 A1 | 7/2006 | Kahn et al. | |
| 2008/0025877 A1 | 1/2008 | Alley | |
| 2009/0100944 A1 | 4/2009 | Newby | |
| 2009/0104692 A1 | 4/2009 | Bartfeld et al. | |
| 2009/0104699 A1 | 4/2009 | Newby et al. | |
| 2009/0105611 A1 | 4/2009 | Wilkinson et al. | |

FOREIGN PATENT DOCUMENTS

| | | |
|---|---|---|
| EP | 0125996 B1 | 7/1987 |
| EP | 0332753 A1 | 9/1989 |
| EP | 1154301 A1 | 11/2001 |
| EP | 1346692 A1 | 9/2003 |
| GB | 1234044 A | 6/1971 |
| GB | 2278441 A | 11/1994 |
| JP | 59113886 A | 6/1984 |
| JP | 61502560 A | 11/1986 |
| JP | 10281953 A | 10/1988 |
| JP | 06078746 A | 3/1994 |
| JP | 2000510703 A | 8/2000 |
| JP | 2001-194365 A | 7/2001 |
| JP | 2001-228063 A | 8/2001 |
| JP | 2003057232 A | 2/2003 |
| JP | 2004-069509 A | 3/2004 |
| JP | 2007508569 A | 4/2007 |
| JP | 2009507231 A | 2/2009 |
| JP | 4965889 B2 | 7/2012 |
| WO | 03031065 A1 | 4/2003 |
| WO | 03044488 A1 | 5/2003 |
| WO | 03/097240 A2 | 11/2003 |
| WO | 2006041297 A2 | 4/2006 |
| WO | 2006/113854 A2 | 10/2006 |
| WO | 2007016935 A1 | 2/2007 |
| WO | 2007028202 A1 | 3/2007 |
| WO | 2008040812 A1 | 4/2008 |

\* cited by examiner

MULTI-CHAMBERED TISSUE CONTAINMENT SYSTEM FOR MOLECULAR AND HISTOLOGY DIAGNOSTICS

CROSS REFERENCE TO RELATED APPLICATION

This application is a divisional application of U.S. Utility application Ser. No. 13/864,447, filed Apr. 17, 2013, now U.S. Pat. No. 8,802,038, entitled "Multi-Chamber Tissue Containment System for Molecular and Histology Diagnostics" which is a continuation application of and claims priority to U.S. Pat. No. 8,449,844, filed Oct. 23, 2008, entitled "Multi-Chambered Tissue Containment System for Molecular and Histology Diagnostics", which claims priority to U.S. Provisional Patent Application No. 60/982,062, filed Oct. 23, 2007, entitled "Multi-Chambered Tissue Containment System For Molecular and Histology Diagnostics", the entire disclosures of each of which are herein incorporated by reference.

BACKGROUND OF THE INVENTION

Field of the Invention

The present invention relates to a container for storing a biological sample. More particularly, the present invention relates to a container for storing a biological tissue specimen in a reagent or, if so desired, in multiple reagents for molecular or diagnostic testing and/or histological testing.

Description of Related Art

Biological samples are often obtained by a researcher or clinician for diagnostic evaluation to determine the presence of certain diseases and to determine an appropriate treatment for the disease. Tissue samples are often obtained from a patient for molecular diagnostic and nucleic acid analysis, particularly RNA and DNA analysis, which have become common place in research for the treatment of numerous diseases. An essential requirement for accurate RNA and DNA analysis is the presence of high quality and intact RNA and DNA within the biological sample.

Oftentimes, the histologic or cytologic analysis will be performed immediately after the sample is removed from the patient or source to avoid molecular changes that may occur during storage. These changes, such as gene transcription, result from the degradation of the nucleic acids within the sample caused by exposure of an untreated sample to certain environmental stresses. However, analysis of the sample immediately after the sample is collected is often impossible or impractical. Therefore, it is necessary to provide a system for storing a sample under controlled conditions for a certain period of time while maintaining the structural and molecular integrity of the sample.

Traditionally, one way of accomplishing this storage is by submerging the sample in a single fixative reagent. A typical fixative reagent is 10% formalin but may also include water, miscible alcohols, ethanol/acetone mixtures, and ethanol/acetic acid mixtures. The containers used for such storage are generally composed of a single integral cavity which could house an effective volume of reagent to treat a particular biological tissue sample. The biological tissue sample is placed in the container along with the reagent, the container is closed, and the sample is then stored and transported while being preserved by the fixative agent. An example of such a container can be seen in U.S. Pat. No. 7,147,826 to Haywood et al. Such containers have experienced some success in the industry, but are subject to certain limitations.

SUMMARY OF THE INVENTION

In accordance with an embodiment of the present invention, a container assembly for storing a biological sample comprises a container extending between a first end and a second end and including a first chamber having a sidewall extending between an open end and a closed end, defining a first chamber interior adapted to receive a sample holder therein. The container also includes a second chamber having a sidewall extending between an open end and a closed end, defining a second chamber interior adapted to subsequently receive the sample holder therein. The second chamber interior is in fluid isolation from the first chamber interior. The container also includes a removable closure for engagement with the first end of the container for enclosing at least one of the open end of the first chamber and the open end of the second chamber while the sample holder is disposed within one of the first chamber interior and the second chamber interior.

In one configuration, the sample holder is detachably connected to the closure. In another configuration, the sample holder is rotatable with respect to the closure. A platform may optionally be attached to the closure and adapted for receiving the sample holder. The platform may be rotatable with respect to the closure.

The sample holder may include a closable housing defining an internal cavity for holding a biological sample. The housing may include a plurality of fluid openings adapted for allowing a fluid disposed within at least one of the first chamber interior and the second chamber interior to pass into the internal cavity. In a further configuration, the sample holder is a histology cassette.

The closure and the container may be threadably matable. Optionally, the closure may include a seal that is engageable with a perimeter of at least one of the open end of the first chamber and the open end of the second chamber to form a liquid impermeable seal therewith. The container may define a longitudinal axis, and the first chamber may be disposed on a first side of the longitudinal axis and the second chamber may be disposed on an opposing second side of the longitudinal axis. The sidewall of the first chamber and the sidewall of the second chamber may conjoin to establish an outer sidewall of the container. In a further configuration, the container has a first end and a second end, and the closure engages the first end of the container and encloses the open end of the first chamber and the open end of the second chamber.

The container may also include a visual indicator for differentiating the first chamber from the second chamber. The visual indicator may be a label selectively positioned on an exterior surface of the container. Alternatively, the visual indicator may be co-formed with a portion of the container. The visual indicator may be integrated with the container adjacent at least one of the open end of the first chamber and the open end of the second chamber. Optionally, the visual indicator is an alphanumeric representation.

The first chamber interior of the container may have a first intended fill volume and the second chamber interior of the container may have a second intended fill volume. The second intended fill volume may be different from the first intended fill volume. The container may also include a first fluid disposed within the first chamber interior, and a second fluid disposed within the second chamber interior. The first fluid may be different than the second fluid. In another configuration, the container may include a fluid disposed within the first chamber interior having a first concentration, and a fluid disposed within the second chamber interior having a second concentration. The first concentration may be different than the second concentration.

The closure of the container may be a membrane enclosing at least one, of the open end of the first chamber and the open end of the second chamber. Alternatively, the container may include both a closure and a membrane enclosing at least one of the open end of the first chamber and the open end of the second chamber. The membrane may be partially removable or pierceable.

In accordance with another embodiment of the present invention, a container for storing a biological sample includes a first end, a second end, and a sidewall extending between the first end and the second end defining a container interior. The container also includes a first chamber defined within the container interior and having an opening adjacent the first end of the container. The container further includes a second chamber defined within the container interior having an opening adjacent the first end of the container. The second chamber is in fluid isolation from the first chamber. The container also includes a closure for sealingly engaging the first end of the container and includes a sample holder for storing a biological sample therein. The closure is adapted to engage the container in a first orientation in which the sample holder is received within the first chamber, and a second orientation in which the same sample holder is subsequently received within the second chamber.

In a further configuration, the sample holder is rotatable with respect to the closure. The sample holder may include a closable housing defining an internal cavity for holding a biological sample. The housing may include a plurality of fluid openings adapted for allowing a fluid disposed within at least one of the first chamber and the second chamber to pass into the internal cavity. In a particular configuration, the sample holder is a histology cassette.

The closure may also include a seal engageable with a perimeter of at least one of the opening of the first chamber and the opening of the second chamber to form a liquid impermeable seal therewith. In yet another configuration, the container may also include a visual indicator for differentiating the first chamber from the second chamber. The visual indicator may be a label selectively positioned on an exterior surface of the container. The visual indicator may also be co-formed with a portion of the container.

Optionally, the container may include a first fluid disposed within the first chamber, and a second fluid disposed within the second chamber. The first fluid may be different than the second fluid. Alternatively, the container may include a fluid disposed within the first chamber having a first concentration, and a fluid disposed within the second chamber having a second concentration. The first concentration may be different than the second concentration. The container may also include a membrane enclosing at least one of the opening of the first chamber and the opening of the second chamber.

In accordance with yet another embodiment of the present invention, a method of housing a biological sample includes the step of providing a container having a first chamber having a sidewall extending between an open end and a closed end defining a first chamber interior. The first chamber interior includes a first fluid disposed therein. The container also includes a second chamber having a sidewall extending between an open end and a closed end defining a second chamber interior. The second chamber interior includes a second fluid disposed therein. The first fluid is different from the second fluid, and the second chamber interior in fluid isolation from the first chamber interior. The method also includes the step of inserting a sample holder into the first chamber interior. The method further includes the step of subsequently transferring the sample holder into the second chamber interior.

Optionally, the method further includes the step of threadedly engaging a closure, having the sample holder detachably connected thereto, with a portion of the container while the sample holder is disposed within at least one of the first chamber interior and the second chamber interior.

In a further embodiment, a support assembly for supporting a sample holder adapted to contain a biological sample therein is provided. The support assembly includes a receiving member having a frame adapted for receiving the sample holder therein, with the frame including structure for engaging the sample holder and supporting the sample holder within the frame. The support assembly also includes a platform connected with the receiving member and supporting the receiving member, with the platform adapted to engage with a container such that the sample holder received within the receiving member extends within an interior portion of the container. The platform is preferably adapted to engage with the container in a first position such that the sample holder received within the receiving member extends within a first interior portion of the container and in a second position such that the sample holder received within the receiving member extends within a second interior portion of the container. The frame may include at least one opening adapted for permitting fluid to flow through the frame and contact the sample holder supported by the frame. Further, the platform desirably extends transverse to the receiving member.

Desirably, the receiving member releasably receives the sample holder therein. Further, the receiving member may include as least one finger for engagement with the sample holder for supporting the sample holder within the frame of the receiving member. Such finger is adapted to exert a biasing force against the sample holder for maintaining and supporting the sample holder within the frame of the receiving member. In certain embodiments, the receiving member of the support assembly may include a plurality of fingers for engagement with the sample holder, at least one of the fingers being adapted to exert a biasing force against the sample holder for maintaining and supporting the sample holder against the frame of the receiving member. In this manner, the plurality of fingers is adapted for maintaining and supporting a plurality of sample holders of various sizes and shapes against the frame of the receiving member.

In yet a further embodiment, a closure assembly is provided for enclosing a container, the closure assembly including a support assembly as noted above. In such a closure assembly, the platform interconnects the receiving member to the closure assembly. The platform is preferably rotatably supported on the closure assembly, and the closure assembly may be threadably engageable with the container, such that threading the closure onto the container can be accomplished while the platform is maintained in a specified position within the container.

A further embodiment contemplates a sample holder receiving member including a generally planar frame comprising a plurality of confining surfaces, the confining surfaces capable of confining a tapered end of a sample holder and a non-tapered end of a sample holder. The member further includes a least one, and preferably a plurality of cantilevered fingers extending from the frame, the cantilevered fingers being deflectable from a less stressed state to a more stressed state when a sample holder is engaged within the confining surfaces, thereby maintaining the sample holder within the frame of the receiving member. At least one of the confining surfaces may be a confining latch, the confining latch deflectable to accommodate an edge of the sample holder, such as the tapered end of a sample holder.

In a further embodiment of the invention, an assembly includes a sample holder in the form of a histology cassette comprising a cavity selectively enclosable by a door, the histology cassette further comprising a tapered end and a non-tapered end. The assembly further includes a receiving member for removably receiving the sample holder, with the receiving member comprising at least one deflectable surface extending from a receiving member base frame, wherein the at least one deflectable surface temporarily positions the sample holder with respect to the receiving member when the sample holder is positioned within the receiving member. The door of the sample holder is capable of being opened with respect to the cavity while the sample holder is positioned within the receiving member.

Further details and advantages of the invention will become apparent upon reading the following detailed description in conjunction with the accompanying drawing figures, wherein like parts are designated with like reference numerals throughout.

DETAILED DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The container of the present invention allows for storage of a biological sample, such as a tissue sample for molecular and histology diagnostics, and in particular histopathology testing. Particularly, the container includes an open end and a closed end, with the interior of the container including a first chamber and a second chamber in fluid isolation from each other. Accordingly, a liquid medium may be contained in at least one of the chambers, such as the second chamber. In this manner, a tissue sample contained in, for example, the first chamber may be handled or processed prior to contacting the tissue with the solution in the second chamber. As will be discussed in greater detail herein, in one embodiment of the invention, the first chamber may be empty representing a storage chamber, and the second chamber may include a liquid medium, such as a reagent in the form of a tissue fixative solution for fixing a sample for histopathology diagnostics. In this manner, a tissue sample may be placed within the first chamber, and when desired, the sample may be thereafter repositioned to the second chambers so as to place the tissue sample in fluid contact with the solution within the second chamber. Alternatively, the first chamber may include a reagent therein with the second chamber being empty, such that the tissue sample may be first placed in the first chamber including the reagent, and after the tissue sample is in contact with the reagent for a desired time period, the tissue sample may be thereafter transferred to the empty second chamber for storage and further analysis.

In a further embodiment of the invention, the first chamber may contain a first solution or reagent, such as a tissue fixative solution, and the second chamber may contain a second solution or reagent, such as a nucleic acid stabilization solution, such that a tissue sample may be placed in the first chamber in fluid contact with the first solution for a desired time period, after which time the tissue sample may be repositioned to the second chamber so as to place the tissue sample in fluid contact with the solution within the second chamber. The embodiments described herein are representative of containers capable of use in any of these manners.

Figure 1:
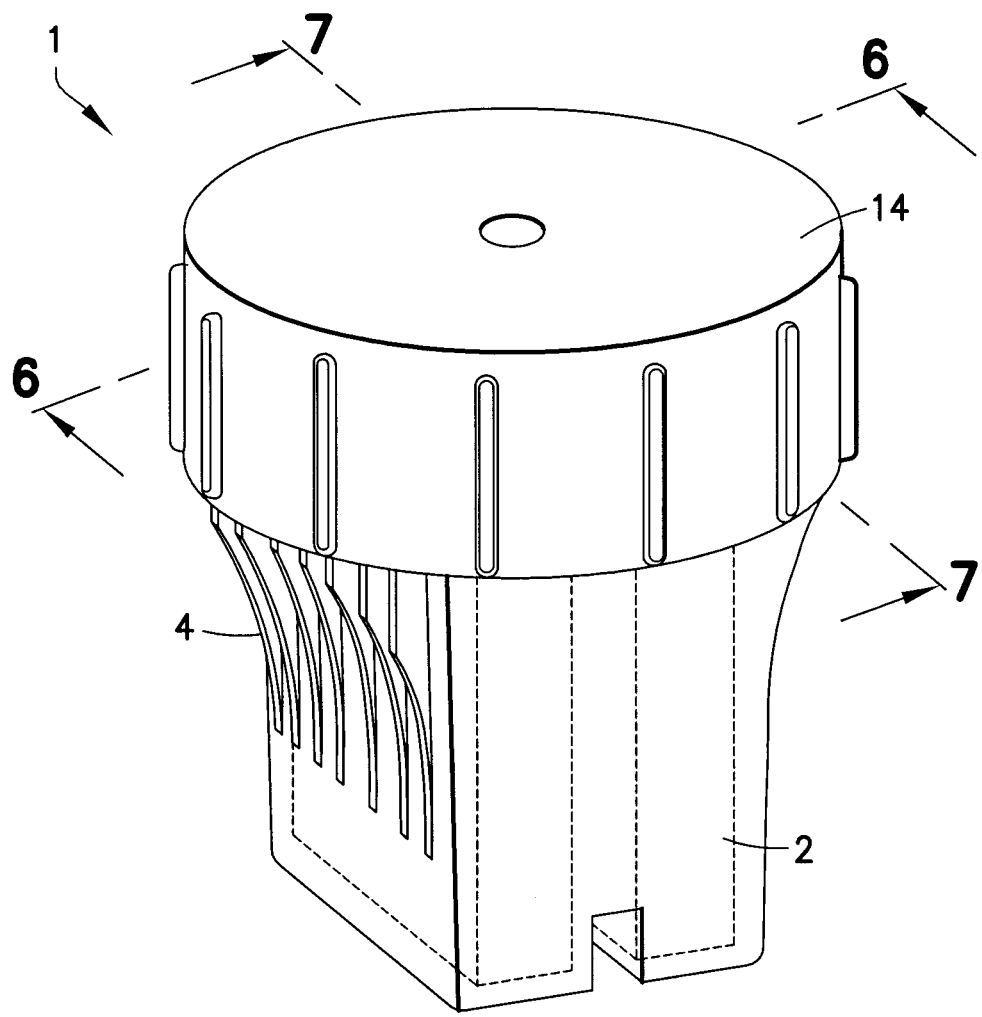
FIG. 1 is a perspective view of a container for storing a biological tissue sample in accordance with one embodiment of the invention.
Figure 2:
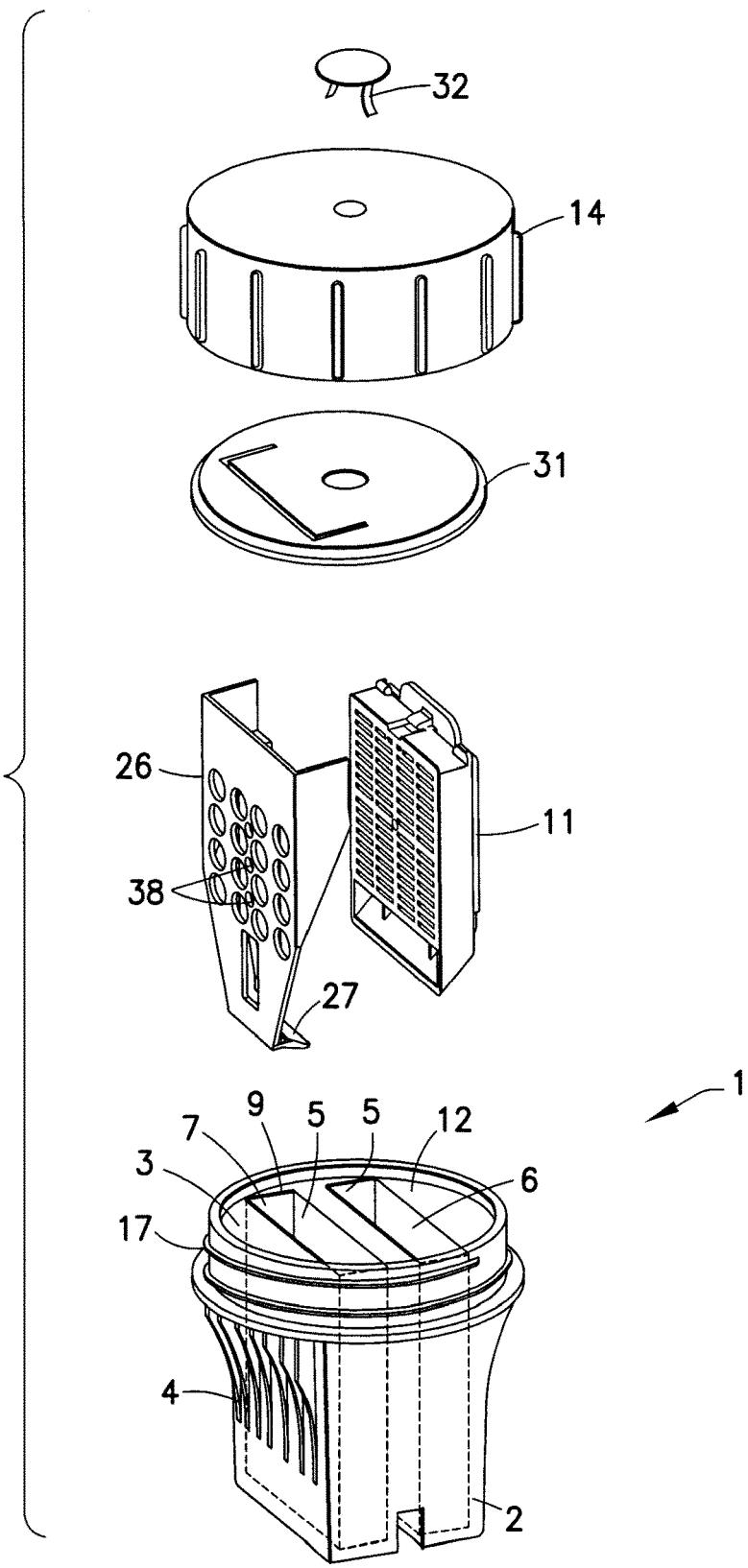
FIG. 2 is an exploded perspective view of the container of FIG. 1.
Figure 3:
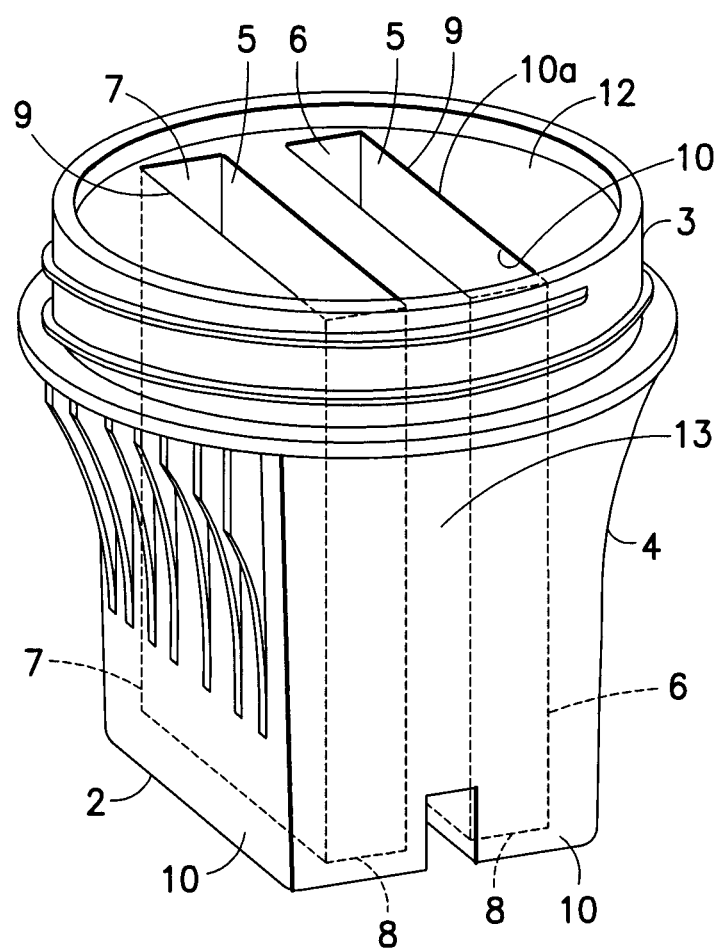
FIG. 3 is a perspective view of the container housing of the container of FIG. 1.

Referring to the drawings, in which like reference characters refer to the like parts throughout the several views thereof, FIGS. 1-3 generally depicts a container 1 for the storage of a biological tissue sample. Container 1 generally includes a first end at container bottom 2, a second end at container top 3, and an outer sidewall 4 extending between container top 3 and container bottom 2, defining a container interior 5. Container interior 5 includes a first chamber 6 having a first chamber interior, and a second chamber 7 having a second chamber interior, housed within container 1. In one embodiment as depicted in FIG. 1, container 1 has a squared shape having arced finger receiving portions disposed on opposing sides of the container 1. It is also contemplated herein that the container 1 can be formed as any shape consistent with the intended use of the description herein.

Figure 10:
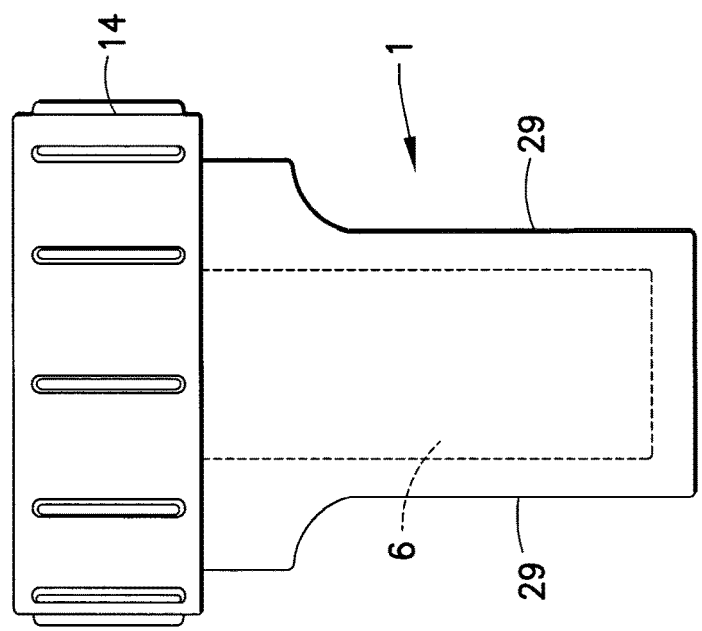
FIG. 10 is a side view of the container of FIG. 9, shown with a closure over the top end of the container.
Figure 9:
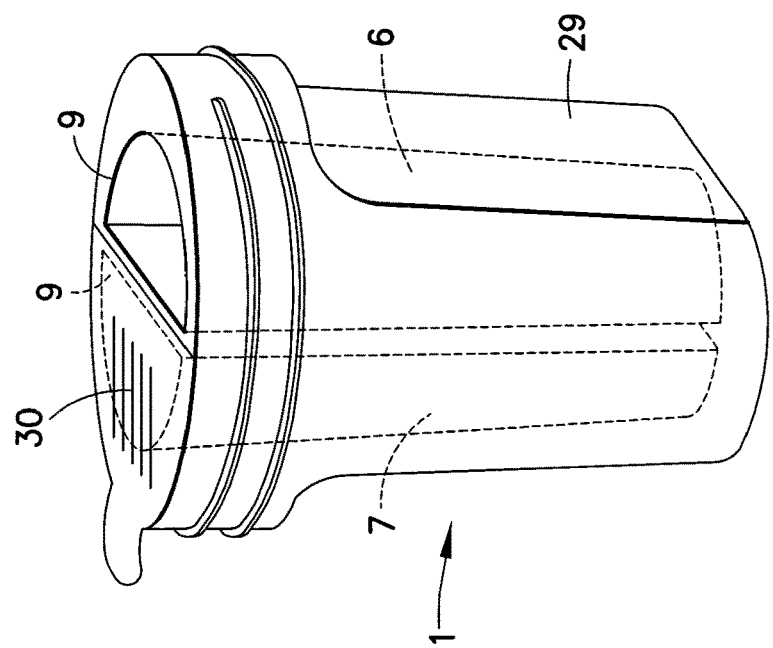
FIG. 9 is a perspective view of a container in accordance with a further embodiment of the present invention.

For example, in an alternate embodiment shown in FIGS. 9-10, the exterior of container 1 may include at least one, and desirably a pair of flat sides 29, thereby providing a surface which can be easily grasped by a user, or to which a label may be affixed, the flat side making it easier to write on the label. Container 1 may be constructed of any known material, such as glass or plastic, and is desirably molded of a polymeric material. Container bottom 2 is preferably flat, so that container 1 can be placed upright on a surface such as a table or lab bench. However, container bottom 2 can alternatively take on other shapes, such as, for example, a cone shape for being received within a corresponding holding apparatus. Container top 3 is also preferably flat, but may take on other shapes as well.

Referring again to FIGS. 1-3, the container interior 5 includes at least two chambers, such as first chamber 6 and second chamber 7. First chamber 6 and second chamber 7 have a hollow cavity defined by a closed end 8, an open end 9, and a chamber sidewall 10 extending from closed end 8 to open end 9. In one embodiment, first chamber 6 and second chamber 7 have a substantially rectangular cross-section extending the entire length of the cavity, however, it is also contemplated that the first chamber 6 and second chamber 7 may have other cross-sectional shapes, such as a circle or a square. As will be described in more detail herein, each of first chamber 6 and second chamber 7 are dimensioned so as to be able to receive and accommodate a same sample holder 11, shown in FIGS. 2 and 4A-4B, therein. Furthermore, the overall size of first chamber 6 and second chamber 7 can be varied to meet the expected volumetric size of sample holder 11 to be contained within first chamber 6 and second chamber 7.

In one embodiment, as shown in FIG. 3, at least a portion of the chamber sidewalls 10 extend to container bottom 2 such that the closed ends 8 of first chamber 6 and second chamber 7 are integrated with, and form a portion of, container bottom 2. Alternatively, the closed ends 8 of first chamber 6 and second chamber 7 may be independent of container bottom 2, such that chamber sidewalls 10 do not extend to the container bottom 2. Referring again to FIG. 3, the open ends 9 of first chamber 6 and second chamber 7 are unobstructed so that a user can access first chamber 6 and second chamber 7 therethrough. In one embodiment, the chamber sidewalls 10 extend to outer sidewall 4 of container 1 so that chamber sidewalls 10 form a portion of container sidewall 4. In this embodiment, chamber sidewalls 10 of first chamber 6 and second chamber 7 conjoin to form the outer container sidewall 4. The top surface of container 1 may form a planar surface with open ends 9 of first chamber 6 and second chamber 7 extending therethrough. For example, as shown in FIG. 3, the top portion 10a of the chamber sidewalls 10 are separated from the outer container sidewall 4, with planar surface 12 extending between the top portion 10a of the chamber sidewalls 10 and the container sidewall 4 adjacent the container top 3.

First chamber 6 and second chamber 7 are provided within container 1 in fluid isolation from one another. For example, a barrier 13 may be disposed between the first chamber 6 and second chamber 7. Barrier 13 may be created between first chamber 6 and second chamber 7, such as by chamber sidewalls 10 representing a common sidewall between first chamber 6 and second chamber 7, or by first chamber 6 and second chamber 7 being distinct chambers having separate wall structures. By providing the first chamber 6 and second chamber 7 in fluid isolation, the user is able to place a different liquid or solution within in each of the chambers without the inadvertent mixing of the liquids or solutions. While first chamber 6 and second chamber 7 can be formed of any known material, desirably first chamber 6 and second chamber 7 are integrally formed from the same material as container 1.

In one embodiment, the first chamber 6 and the second chamber 7 may be disposed within the container 1 in a substantially parallel orientation with respect to each other. This orientation is represented in the cross-sectional view of FIG. 6, in which the longitudinal axis of the first chamber 6, represented by line A-A, and the longitudinal axis of the second chamber 7, represented by line B-B, are parallel. With respect to the positioning of first chamber 6 and second chamber 7 within container 1, in the embodiment shown in FIG. 6, container 1 has a central longitudinal axis, shown by line C-C, and first chamber 6 is disposed entirely on a first side of a plane dissecting the axis C-C while second chamber 7 is disposed entirely on a second opposing side of the same plane dissecting this axis C-C. It is also contemplated herein that the first chamber 6 and second chamber 7 may be disposed on the same side of a plane dissecting longitudinal axis C-C of container 1.

Figure 5:
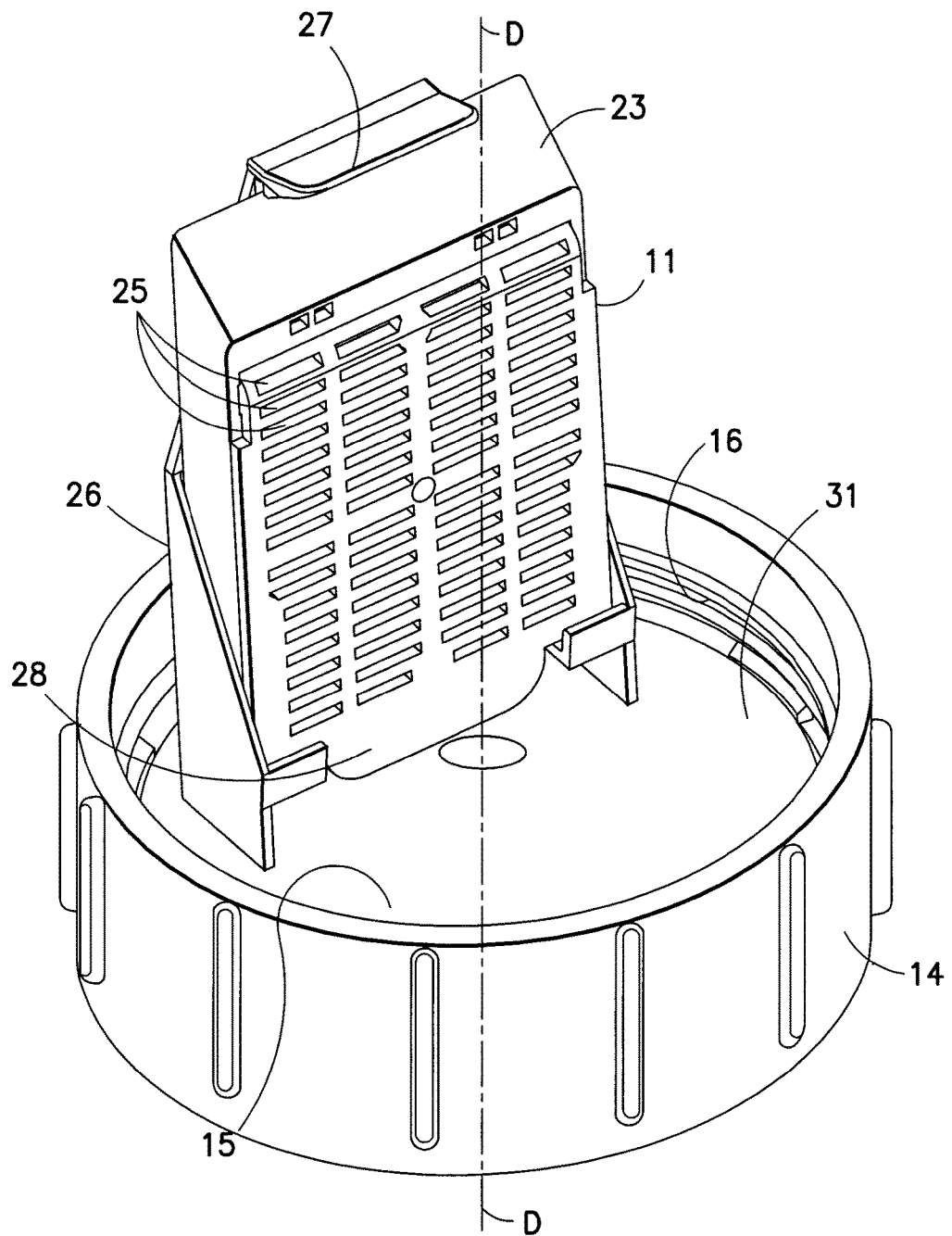
FIG. 5 is a perspective view of the bottom of the closure of FIG. 1 having the sample holder attached thereto.

In one embodiment, shown in FIGS. 2 and 5, the container 1 also includes a cover or closure for enclosing at least one of the open ends 9 of at least one of the first chamber 6 and second chamber 7. The container 1 may include a distinct closure 14 represented as a cap or lid, preferably constructed of a molded polymer material for mating with the container top 3. Closure 14 may engage the container 1 at container top end 3, adjacent which one or more of the open ends 9 are oriented. Closure 14 can engage container 1 in any manner, such as a frictional fit, snap fit, interlocking structural engagement, or other manner, providing a liquid tight seal. Desirably, closure 14 and container 1 include corresponding threads such that closure 14 can be threaded with container 1 to provide a liquid tight seal therebetween. For example, closure 14 as shown in FIG. 5, may be threadably matable with container 1 by way of first threaded members 16 disposed within closure 14 and corresponding second threaded members 17 disposed on the exterior of container 1 near container top 3, as shown in FIG. 2. Alternatively, such corresponding threads may be provided about the perimeter of an external surface of closure 14 and within the perimeter of an internal surface of sidewall 4 of container 1 near container top 3.

In another embodiment, the closure or cover may be a removable or pierceable membrane, such as a foil or wax material, affixed to the top end 3 of container 1 so as to enclose the open ends 9 of first chamber 6 and second chamber 7. A single membrane may enclose the open ends 9 of both first chamber 6 and second chamber 7 in container 1 or, alternatively, multiple membranes can be used, in which each membrane encloses individual open ends 9 of first chamber 6 and second chamber 7, respectively. The membrane can be removed by the user when access to the specific first chamber 6 and/or second chamber 7 is desired.

As shown in FIGS. 9-10, a removable membrane 30 may be provided over one or both of the open ends 9 of first chamber 6 and second chamber 7. For example, as shown in the embodiment of FIG. 9, a removable membrane in the form of a peel-away cover 30, such as a foil or label, may be provided over one of the chambers, such as over second chamber 7.

In this manner, the interior of the first chamber 6 and/or the second chamber 7 may be maintained in a sterile or uncontaminated state during storage prior to use. The peel-away cover 30, such as a foil or label, may be removed from either the first chamber 6 and/or the second chamber 7 immediately prior to use. Such a foil may also provide for differentiation between the first chamber 6 and second chamber 7.

Referring again to FIG. 2, the container 1 is intended to be used in conjunction with a sample holder 11 in order to test, preserve or treat a biological tissue sample housed within sample holder 11. Any suitable sample holder 11 capable of holding a biological tissue sample may be used with container 1. Sample holder 11 is adapted to be received within first chamber 6 of container 1, and is also adapted to be subsequently received within second chamber 7. Sample holder 11 may form a part of closure 14, or may be separately provided for use with container 1. Sample holder 11 may be in the form of a conventional histology cassette (a "histo-cassette") as is known in the art for storing a biological tissue sample during preparation of the sample for diagnostic testing. Such sample holders or histo-cassettes are known for containing biological specimens during processing with fluids to prepare the specimen for later analyses. Typically, such sample holders or histo-cassettes are generally rectangular, planar housing structures having an internal cavity, with a plurality of openings through the wall surface to provide fluid flow through the housing. Often, a removable or openable cover encloses the structure, such as through a hinge situated along one end of the housing structure for providing a door-like cover to the housing structure. Also, a planar surface, which may be slanted, is often provided in such sample holders or histo-cassettes, acting as a surface for labeling or writing. The dimensions for such a sample holder, for example, may include a height of about 0.3 inch (plus or minus 0.1 inch), a length of about 1.73 inches (plus or minus 0.1 inch), and a width of about 1.12 inches (plus or minus 0.1 inch). Examples of sample holders that may be useful herein are shown in U.S. Pat. No. 4,220,252 to Beall et al. and U.S. Pat. No. 4,034,884 to White, both of which are expressly incorporated herein by reference.

Figure 4A:
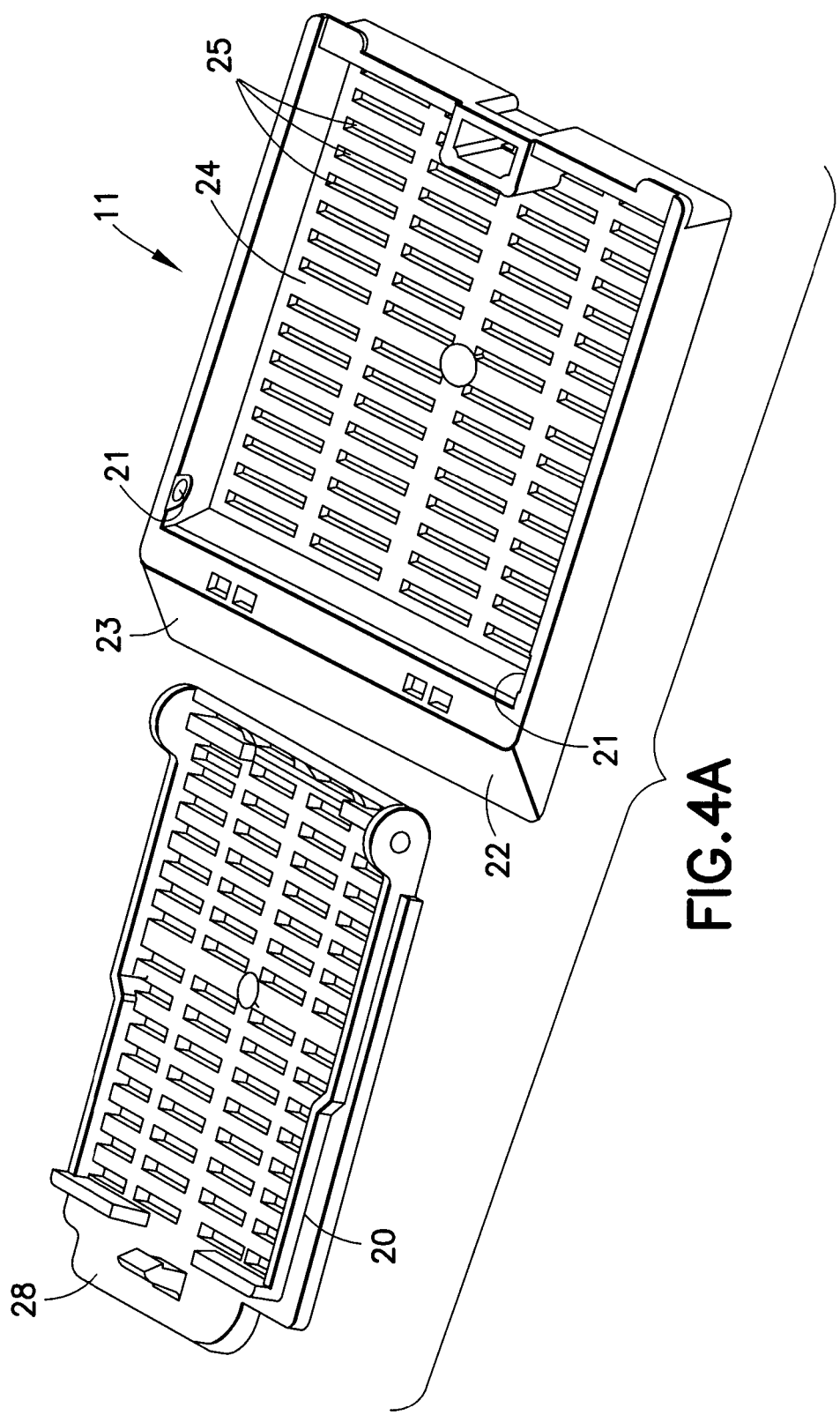
FIG. 4A is a perspective view of one embodiment of a sample holder, shown in an open position.
Figure 4B:
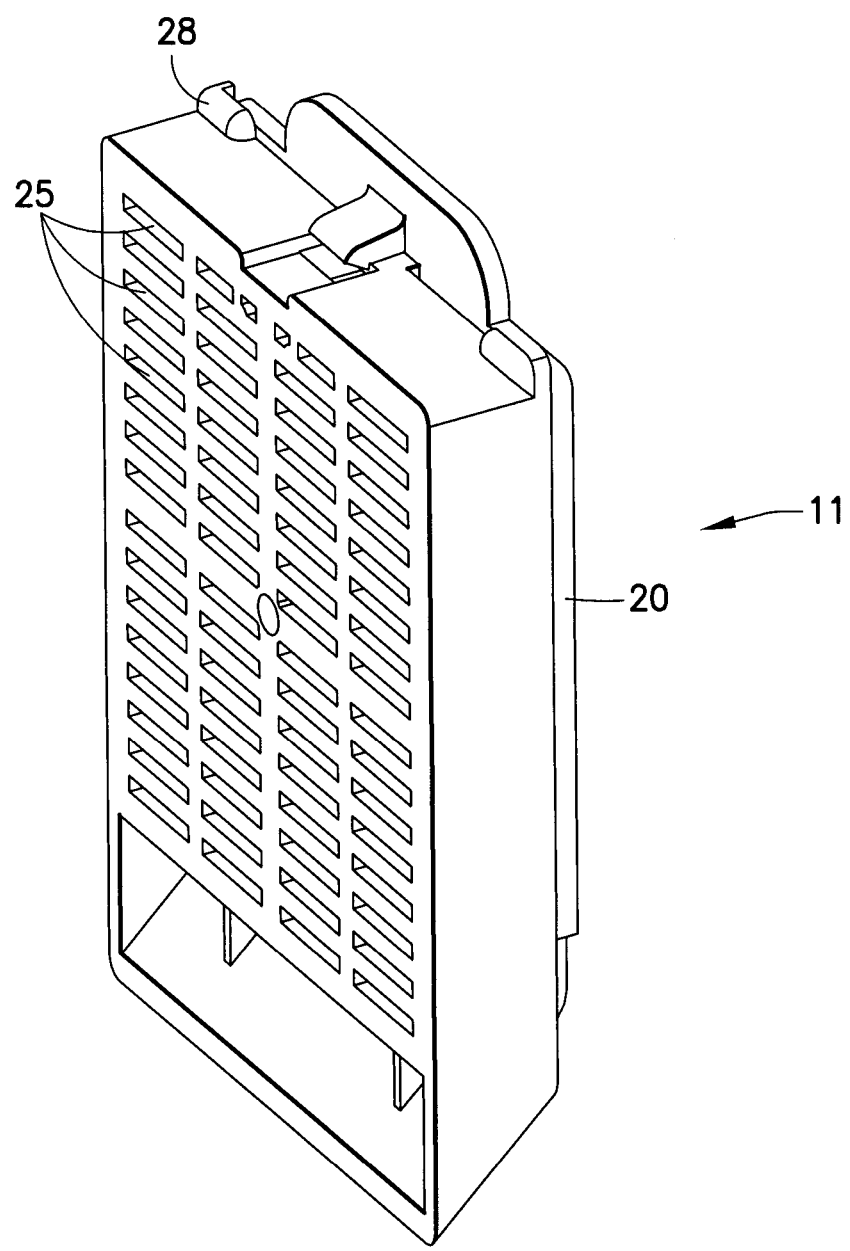
FIG. 4B is a perspective view of the sample holder of FIG. 4A, shown in the closed position.

For example, as shown in FIGS. 4A and 4B, sample holder 11 includes a generally rectangular planar housing 23 having opposing walls defining an internal cavity 24 for holding a biological tissue sample therein. At least one of the walls of housing 23 may be slanted, such as slanted wall 22, providing a surface for applying a label or for writing, so as to provide a mechanism for identification of a sample contained within sample holder 11, as appropriate. Housing 23 of sample holder 11 is a closable structure, and may include a hinged door-like structure 20 attached with housing 23 thereby permitting access to the internal cavity 24 for storing a tissue sample within or removing a tissue sample from internal cavity 24. The door-like structure 20 may be integrally formed with housing 23 so as to provide a unitary structure with the door 20 connected to housing 23 through a flap to provide a mechanism for pivoting door 20 with respect to housing 23, or door 20 may be otherwise connectable to housing 23, such as through a pivot point 21 acting as a hinge for opening door 20 from one side of housing 23 to gain access to the internal cavity 24. Housing 23 of sample holder 11 includes at least one, and preferably a plurality of fluid openings 25 adapted to allow fluid to flow therethrough. In this manner, when housing 23 is positioned within first chamber 6, fluid within first chamber 6 can flow through openings 25 and contact the biological tissue sample contained within internal cavity 24.

Sample holder 11 may be provided as a separate element for use within first chamber 6, or may be interconnected with a part of container 1. An aspect of container 1 relates to limiting the amount of contact a user has with the biological tissue sample and the sample holder 11 in order to avoid contamination of the sample. To limit this contact, container 1 optionally includes structure for mating sample holder 11 with closure 14 so that sample holder 11 can be transferred between first and second chambers 6, 7 through a user's direct contact with the closure 14 only. Desirably, sample holder 11 is mated with closure 14. Such mating may be accomplished by providing sample holder 11 as an integral part connected to or formed with closure 14, or sample holder 11 may be a separate structure that is removably matable or detachably connected with closure 14.

As shown in FIGS. 2 and 5, closure 14 may include a frame or rack element defining a receiving member 26 extending from a bottom surface of closure 14, for accommodating sample holder 11 therein. Receiving member 26 may include structure for maintaining sample holder 11 attached to closure 14 as shown in FIG. 5, such as in a snap-fit engagement, and sample holder 11 may be releasable from receiving member 26. In particular, receiving member 26 may include structure defining a rectangular recess for accommodating the general size and shape of sample holder 11. Receiving member 26 may include at least one confining latch or finger 27 extending therefrom for engaging with an edge of sample holder 11, thereby maintaining sample holder 11 within the recess defined by receiving member 26. Such finger 27 may be deflectable, such that when an edge of sample holder 11 is held in place against a corresponding wall surface of the receiving member 26, and sample holder 11 is pushed into the recess of receiving member 26, finger 27 deflects away from the wall of sample holder 11 and then returns at least partially towards an initial position, thereby snapping sample holder 11 in place. Finger 27 is desirably deflectable such that sample holder 11 may be removed from receiving member 26 when desired.

It is further contemplated that receiving member 26 may also be provided with a general shape so as to permit opening of door 20 of sample holder 11 while maintaining housing 23 of sample holder 11 contained therein, thereby providing access to the interior cavity 24 of sample holder 11 while sample holder 11 is held in place within receiving member 26 and with respect to closure 14. For example, receiving member 26 may have a wall cut-away portion 50 to accommodate a handle-like protrusion 28 of door 20, and the overall dimensions and height of the walls of receiving member 26 may be designed so as to provide for manually opening of the door 20 by contact of handle 28 and pivoting of door 20 across receiving member 26 without interference. Receiving member 26 may include a plurality of holes 38 to allow a fluid to pass through receiving member 26 to contact the sample holder 11 and the sample contained therein.

The receiving member may include structure making it capable of accommodating histo-cassettes or sample holders of different sizes and shapes. The receiving member 26 may define a frame structure having a general arrangement including a plurality of confining surfaces for receiving and supporting the sample holder thereon. For example, as shown in one embodiment depicted in FIGS. 15A-15E, receiving member 26a may define a frame, and may include cantilevered fingers 40a and 42a, which act as compressible elements for bearing against the wall surfaces of sample holders of various sizes. Such fingers 40a and 42a may be deflectable from a less stressed state to a more stressed state, that is, act as biasing elements or leaf springs for exerting a biasing force against the wall surface of a sample holder placed within receiving member 26a, biasing the sample holder against the sidewalls of receiving member 26a to hold the sample holder in place. More particularly, fingers 40a apply a biasing force against a sample holder contained within receiving member 26a, while opposing surface 41a holds an end of the sample holder therein and finger 27a holds a separate edge of the sample holder therein. Also, finger 42a applies a biasing force against the sample holder while opposing finger 27a holds the end of the sample holder in place. Such opposite and equal forces assist in maintaining sample holders of various sizes and shapes in place. Further, wall cut-away portion 50a may also be provided, for accommodating a handle portion of the door of the sample holder, as discussed above, while also providing access to the handle portion for opening of the door while the sample holder is in place in the receiving member, if desired. In this manner, container 1 may be provided with a single receiving member that can accommodate various sizes and shapes of histo-cassettes therein for use with container 1. Additionally, receiving member 26a may include a plurality of holes 38a for fluid flow therethrough, as discussed above. Such holes 38a may include a pattern or orientation such that fluid flow through the platform to the sample holder will be sufficient for contact with a sample contained within the sample holder regardless of the size, shape and/or geometry of the sample holder.

Referring again to FIGS. 2 and 5, receiving element 26 may be attached to the bottom surface of closure 14 through a platform 31. Platform 31 may be attached to closure 14 so that platform 31 is rotatable with respect to closure 14, such as through a nub extending from platform 31 into closure 14 providing for pivoting engagement therebetween, or alternatively through a pivoting connection 32. In one embodiment, the sample holder 11 can be attached to the platform 31, either directly or through a receiving member 26 connected to platform 31, making sample holder 11 also rotatable with respect to closure 14. Receiving member 26 may be optionally connected with platform 31 through any mechanism, such as through an integrally formed structure, a mechanical connection forming a snap-fit, an adhesive bond, and the like. In the embodiment of FIGS. 15A-15E, receiving member 26a includes a projection at nub 44a, which may be received in a corresponding opening extending in the platform, thereby maintaining receiving member 26a therein in a mechanical inter-engagement, with the platform 31 extending transverse to the receiving member 26a. In this manner, the platform 31 is adapted to engage with the container 1 at the top end thereof, in a first position such that the sample holder that is received and supported within receiving member 26 extended within first chamber 6 of container 1, and in a second position such that the sample holder extends within second chamber 7 of container 1.

Figure 6:
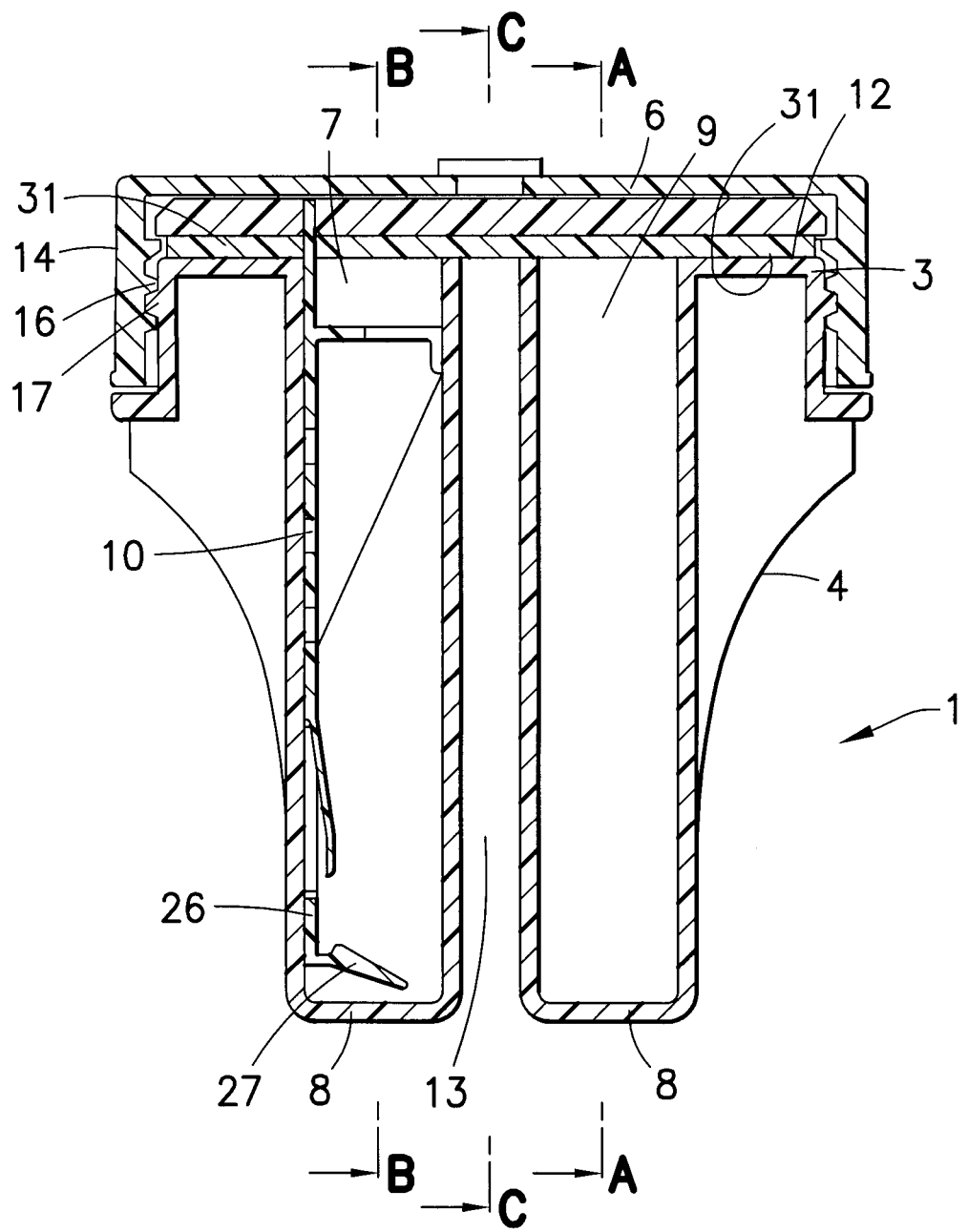
FIG. 6 is a cross-sectional view of the container taken along line 6-6 of FIG. 1, shown without the sample holder therein.

As shown in FIG. 5, the receiving member 26 may be connected with platform 31 in a position and manner which is off-set from the main central axis D-D of the closure 14. Such an off-set orientation provides for appropriate alignment of sample holder 11 within the respective first and second chambers 6, 7 of container 1, in some cases irrespective of orientation of the closure with respect to the first and second chambers 6, 7. In particular, first and second chambers 6, 7 are aligned within container 1 about the central axis C-C of container 1, as shown in FIG. 6. By providing receiving member 26 in a position with respect to platform 31 that is off-set from the central axis C-C, sample holder 11 can be properly contained within the receiving member 26 and placed within either first or second chambers 6, 7 of container 1 with closure 1 properly oriented over the top of container 1. With the rotatable connection between platform 31 and closure 14, when sample holder 11 is inserted into either of first chamber 6 or second chamber 7, one or both of receiving member 26 and/or sample holder 11 will gently contact chamber sidewall 10 upon rotation of closure 14, thereby causing sample holder 11 to rotate with respect to closure 14, and allow closure 14 to threadably engage container 1. This greatly reduces the amount of agitation experienced by a sample housed within the sample holder 11 during engagement of the closure 14 with the housing 1.

Figure 16A:
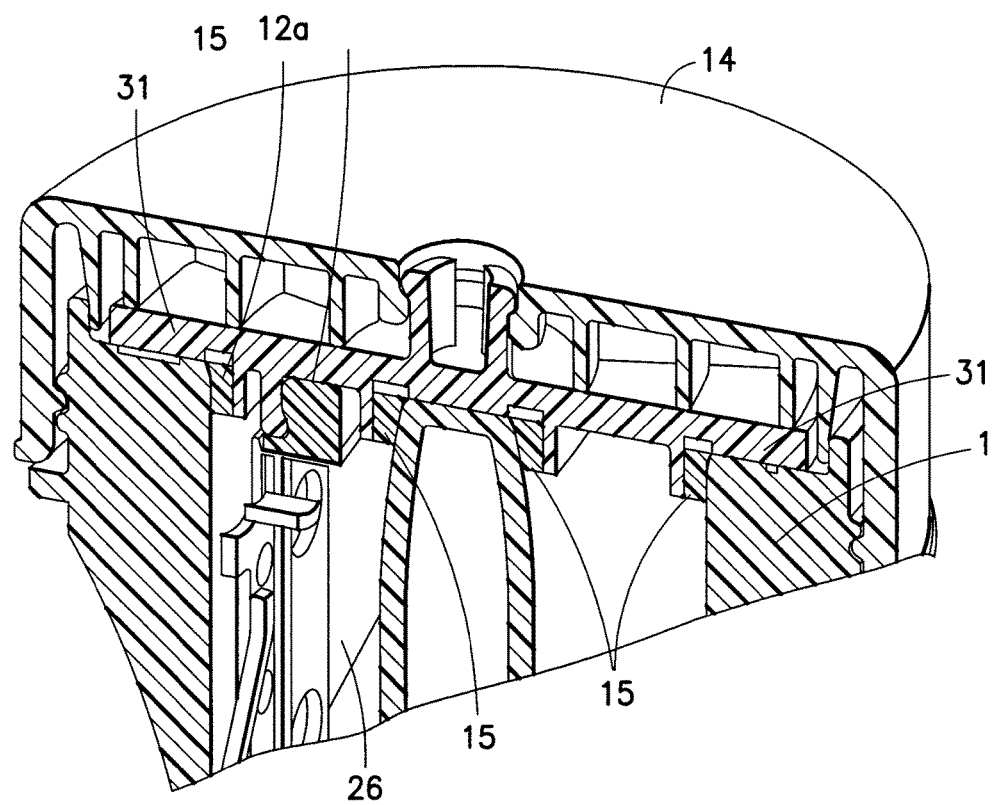
FIG. 16A is a partial schematic cross-sectional view of a container in accordance with an embodiment of the present invention having a portion of the closure and the platform molded thereto.
Figure 16B:
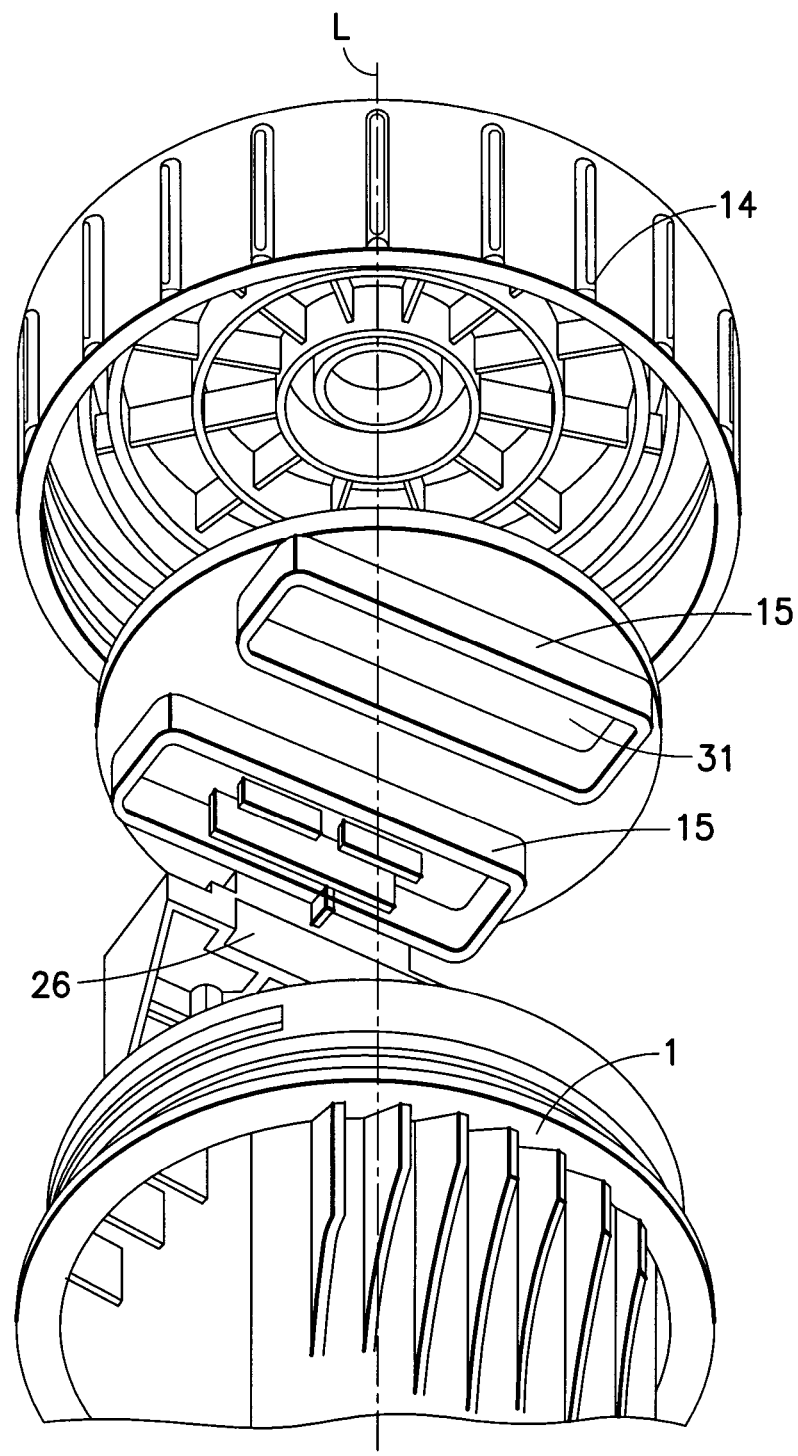
FIG. 16B is a partial exploded perspective of the container of FIG. 16A.

As shown in FIGS. 16A-16B, the platform 31 can also act to provide a fluid-tight seal of closure 14 with respect to container 1. Platform 31 may be constructed of a material adapted to sealingly engage with surface 12 at container top 3 when closure 14 is mated within container 1. For example, at least the bottom surface of platform 31 may be constructed of an elastomeric material, forming seal surface 15 for mating with at least a portion of planar surface 12 of container 1, shown in FIG. 2, when closure 14 is mated with container 1 and engaged therewith. As closure 14 experiences torque during engagement with the container 1, seal surface 15 sealingly engages planar surface 12 to provide a fluid tight seal. Desirably, as seen in the cross-section of FIG. 16A, platform 31 is a two-shot molded material, with seal surface 15 molded from an elastomeric material for providing sealing properties when engagement with container 1, and with the opposing surface 12a constructed of a polymeric material for connection with receiving member 26. In a further embodiment, as shown in FIGS. 16A-16B, the seal surface 15 is engageable with a perimeter of the open end of the first chamber and/or the open end of the second chamber (as previously described) of the container 1 to provide a liquid impermeable seal therewith when the closure 14 is engaged with the container 1. Optionally, the seal surface 15 may be made of a rubberized or otherwise deflectable material to assist in forming a seal with the container 1.

More particularly, in the embodiment represented in FIG. 16B, two separate seal surfaces 15, 15' are provided for respective sealing engagement about the perimeter of the open ends of the first chamber and the second chamber, respectively. Seal surfaces 15, 15' represent first and second perimetrical seals for providing fluid tight engagement with the open ends of the chambers. Moreover, receiving member 26a extends from a surface of platform 31 at a location within the perimeter of seal surface 15'. In this manner, when a sample holder is supported by receiving member 26a and positioned within one of the first chamber or the second chamber, the seal surface 15' seals about the perimeter of the open end of chamber containing the receiving member 26a, and the other seal surface 15 seals about the perimeter of the open end of the other chamber which does not contain the receiving member 26a. As such, seal surfaces 15, 15' from a liquid impermeable seal with the first and the second chambers, respectively. Moreover, seal surfaces 15, 15' are of the same structure, and are therefore adapted to seal either of the first or second chamber. In this regard, when the receiving member 26a is transferred from one chamber to the other chamber during use, the seal surfaces 15, 15' are adapted to be removed from sealing engagement with the initial chamber and to subsequently seal the other chamber.

Figure 19A:
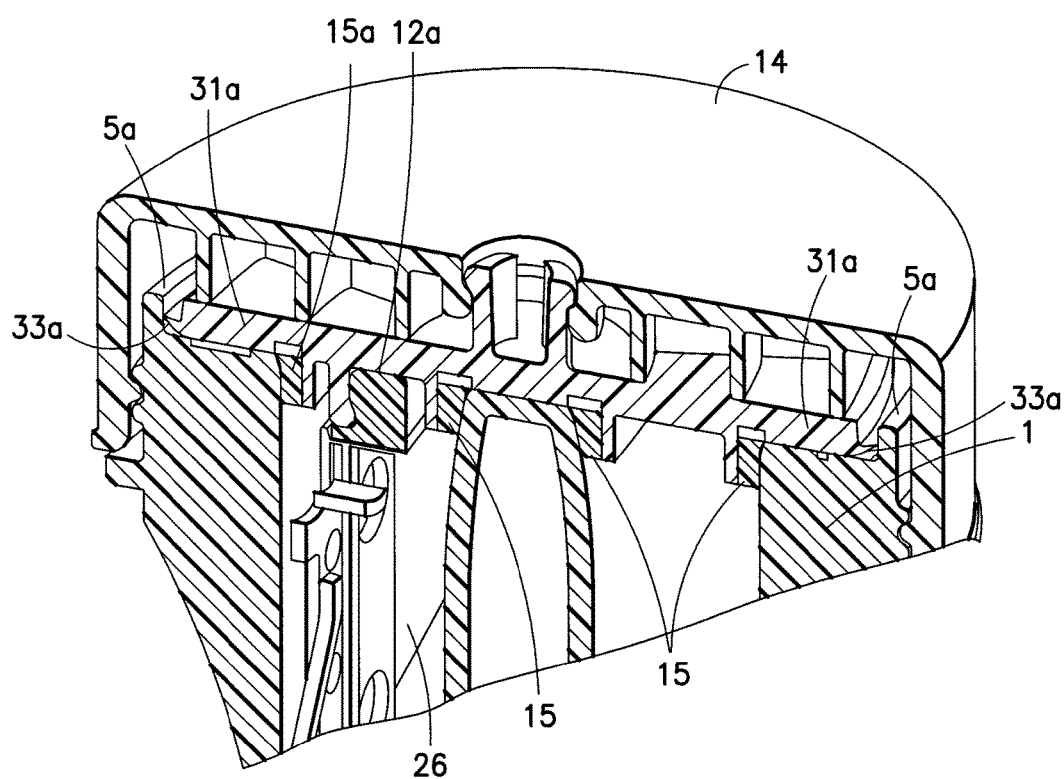
FIG. 19A is a partial schematic section view of a container in accordance with a further embodiment of the invention depicting a perimetrical seal.
Figure 19B:
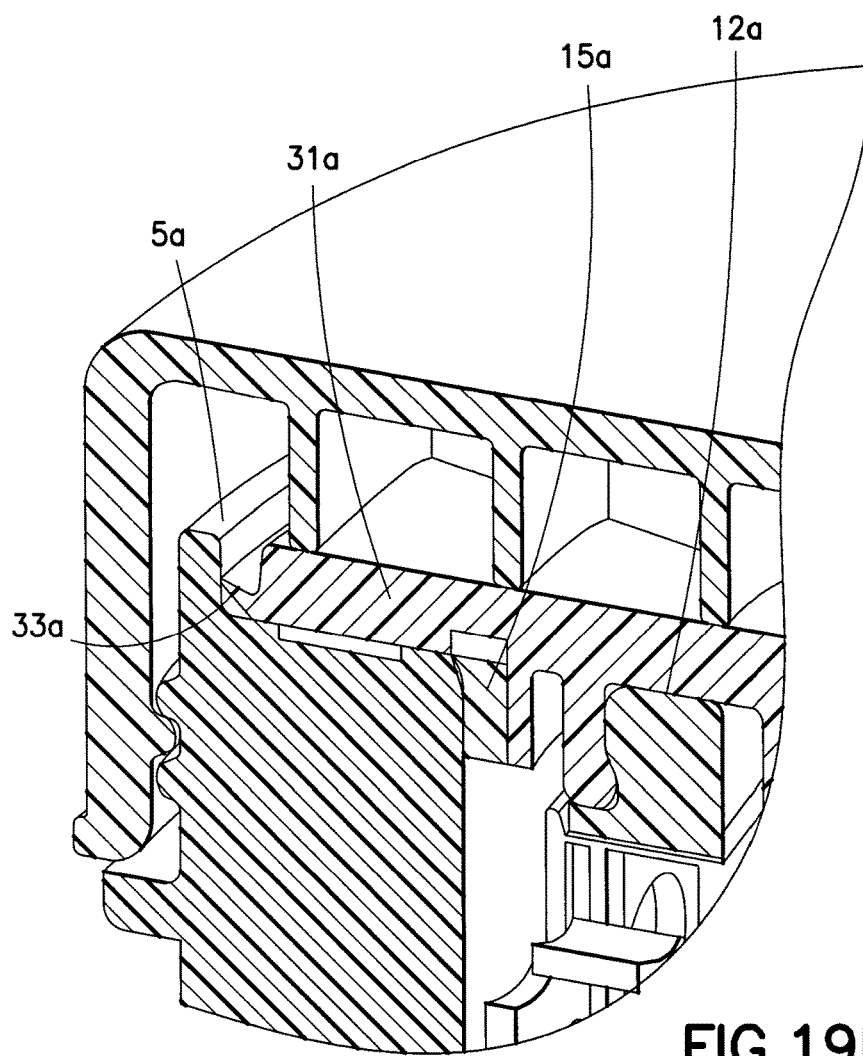
FIG. 19B is an enlarged view of FIG. 19A showing the perimetrical seal in detail.
Figure 19C:
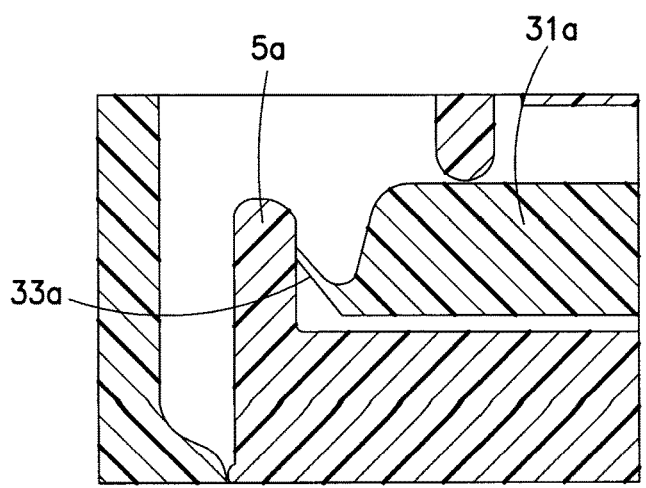
FIG. 19C is a cross-sectional view of FIG. 19B showing the perimetrical seal.

In a further embodiment, the platform may include a further seal element adapted for acting as a seal with respect to the top of container 1. For example, as depicted in FIGS. 19A-19C, platform 31a may include a perimetrical seal 33a extending about the perimeter of platform 31a. Perimetrical seal 33a is adapted for sealing engagement with rim 5a extending about the perimeter of container 1, that is, extending about the perimeter of the container top surface, when closure 14 is mated with container 1. Perimetrical seal 33a may be a separate element connected with or otherwise attached to the perimeter of platform 31a, or may be integrally formed or co-molded therewith. Perimetrical seal 33a is constructed of a material capable of forming a seal surface against rim 5a when closure 14 is mated with container 1. Desirably, perimetrical seal 33a is constructed of a material that is adapted to flex and/or deflect when moved with respect to rim 5a, and is desirably integrally formed with platform 31a of a material that is structurally sound enough to support the platform while being sufficiently flexible to form a perimeter seal. In this manner, as closure 14 is mated with container 1, perimetrical seal 33a engages rim 5a so as to form a fluid tight seal therewith. When closure 14 is mated with container 1, perimetrical seal 33a provides an effective seal with the top of container 1 at rim 5a for providing effective sealing properties between closure 14 and container 1, thereby preventing any fluid from leaking out of container 1 at closure 14. Moreover, perimetrical seal 33a may act as the only independent seal for closure 14, or may work as a secondary seal in conjunction with seal surface 15a in engagement about the perimeter of the open end of the first chamber and/or the open end of the second chamber, as described above.

Referring to FIGS. 11A-11B and 17-18, the container 1 may also be provided with features for differentiation between first chamber 6 and second chamber 7, such as a visual indicator 53. The visual indicator 53 can be disposed at any position on container 1 that is visible to a user. Such an indicator could also be disposed on container sidewall 4. In another embodiment, the indicator could be disposed on one or more than one of the container sidewalls. As examples, the visual indicator 53 can be in the form of an alphanumeric symbol, a line or series of lines, a color differentiation, differential surface finishes, and the like. The visual indicator 53 may be integrated into a membrane covering a particular open end of the first chamber 6 and/or the second chamber 7.

Figure 17:
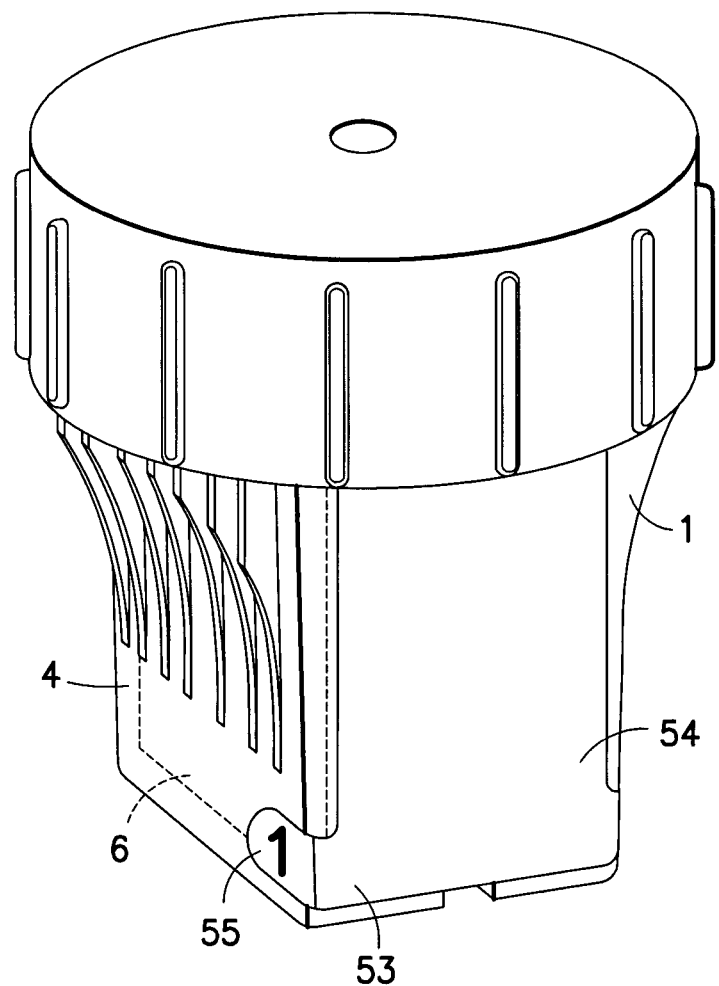
FIG. 17 is a perspective view of a container in accordance with an embodiment of the present invention having a label affixed thereto having identification indicia thereon.
Figure 18:
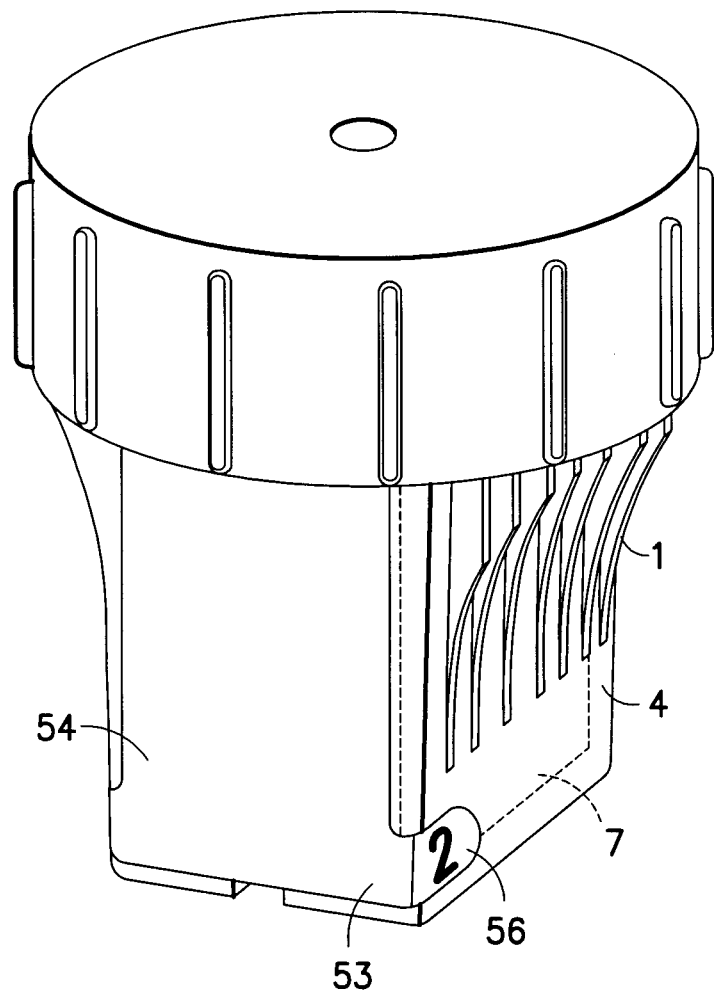
FIG. 18 is an alternative perspective view of the container of FIG. 17.

Alternatively, as shown in FIGS. 17-18, the visual indicator 53 may include a label 54 disposed about a portion of the container sidewall 4 in which a first numeric indicator 55 is physically disposed adjacent the first chamber 6, and a second numeric indicator 56 is physically disposed adjacent the second chamber 7. In one configuration, the same label 54 may include both the first numeric indicator 55 and the second numeric indicator 56. In another configuration, a portion of the container 1, such as a flattened portion of the container sidewall 4, provides a label affixing surface to determine proper alignment of the first numeric indicator 55 and the second numeric indicator 56 of the label 54 onto the container 1.

Figure 11A:
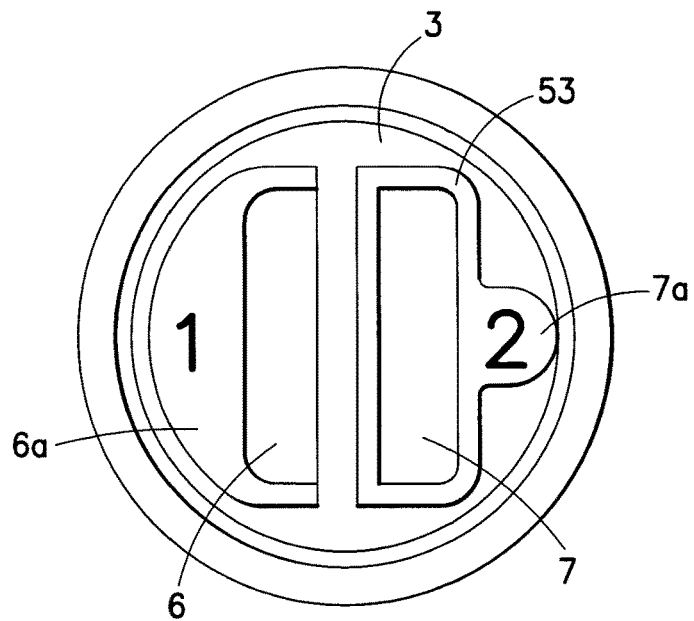
FIG. 11A is a top view of a container in accordance with a further embodiment of the present invention having alphanumeric identification indicia.
Figure 11B:
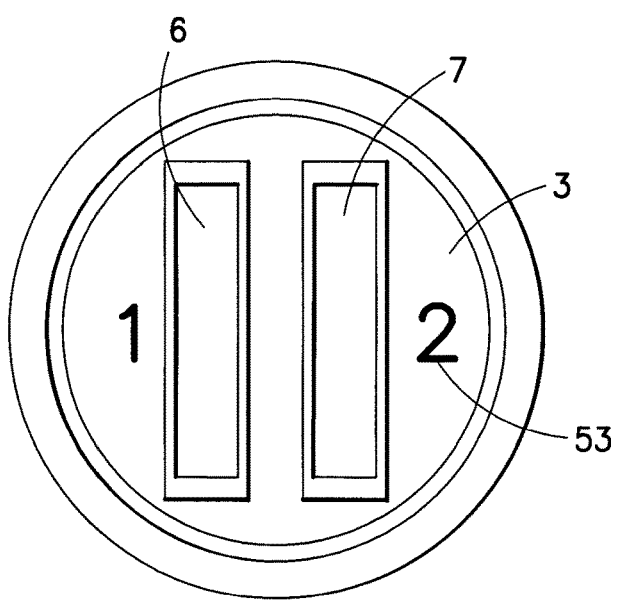
FIG. 11B is a top view of a container in accordance with yet a further embodiment of the present invention also having alphanumeric identification indicia.

In another embodiment, as shown in FIGS. 11A and 11B, visual indicators 53 are disposed on container top 3 near the open end 9 of each of first and second chambers 6, 7. In particular, a visual indicator 53 such as the number "1" (designating, for example, the first step of a procedure) may be used to identify the first chamber 6, and a visual indicator 53 such as the number "2" (designating, for example, the second step of a procedure) may be used to identify the second chamber 7. As in FIG. 11A, the a first visual indicator 53 "1" may be a positive protrusion, forming a bump, which is clearly visible to the user when the closure 14 is removed from container 1 for initial use, while a second visual indicator 53 "2" may be a reversed out recess, which is partially obstructed with a peel-away cover 30, such as a foil or label. Moreover, the portion of container 1 which comprises the first chamber 6 may also include a surface finish of varying and/or visually discernable appearance, such as a frost-like surface, to differentiate the first chamber 6 from the second chamber 7. Such differentiations make it clear to the user which portion of container 10 is meant to be used first.

Figure 12A:
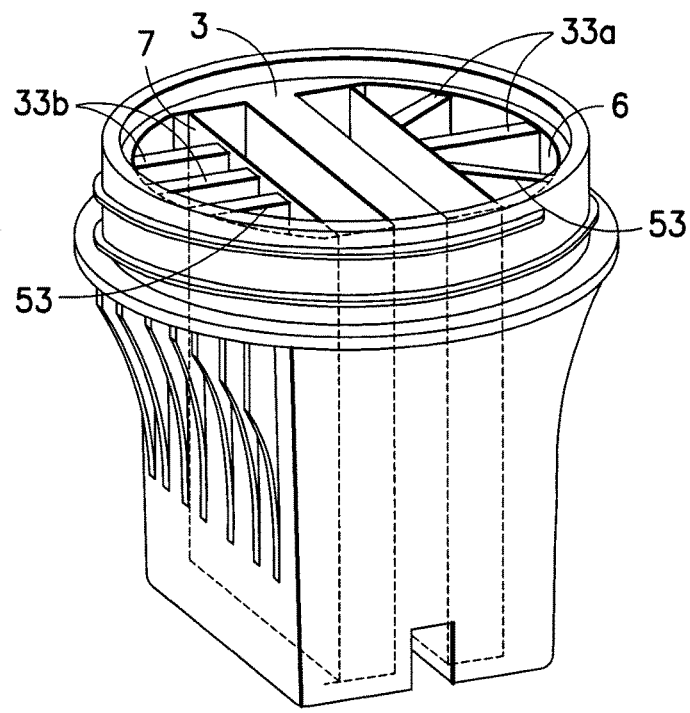
FIG. 12A is a perspective view of a container housing in accordance with a further embodiment of the present invention having structural identification indicia.
Figure 12B:
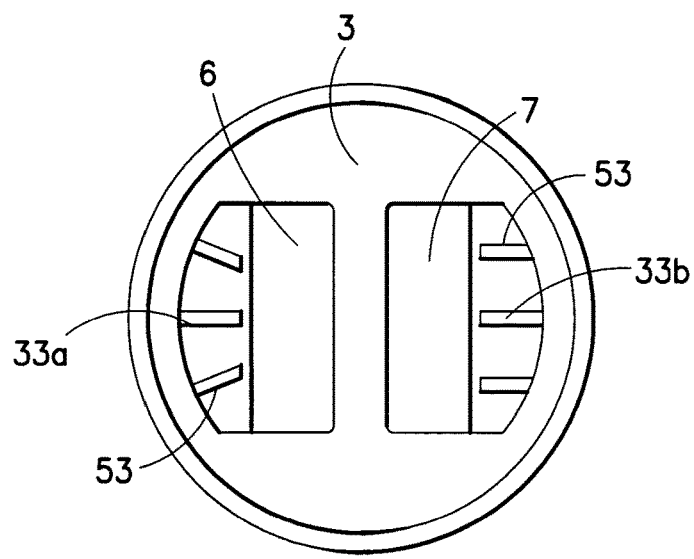
FIG. 12B is a top view of the container housing of FIG. 12A.

Alternatively, as shown in FIGS. 12A-12B, a visual indicator 53 may include a differentiation molded into the container geometry. The precise arrangement of such a visual indicator may take various forms. For example, the container 1 may include ribs 33a extending toward the first chamber 6, and distinct ribs 33b extending toward the second chamber 7 in a direction distinct from ribs 33a. Optionally, a first set of ribs 33a may be disposed adjacent the first chamber 6 having a substantially perpendicular orientation with respect to a sidewall of the first chamber 6, and the second set of ribs 33b may be disposed adjacent the second chamber 7 having a substantially parallel orientation with respect to a sidewall of the second chamber 7. Alternatively, the first set of ribs 33a may be disposed adjacent the first chamber 6 having a substantially parallel orientation with respect to a sidewall of the first chamber 6, and the second set of ribs 33b may be disposed adjacent the second chamber 7 having a substantially perpendicular orientation with respect to a sidewall of the second chamber 7. In yet another configuration, one of the first set of ribs 33a or second set of ribs 33b may be disposed at an angle with respect to a sidewall of one of the first chamber 6 and the second chamber 7, and the other of the first set of ribs 33*a* and the second set of ribs 33*b*, may be disposed a different angle with respect to a sidewall of the other of the first chamber 6 and the second chamber 7. In yet another configuration, one of the first set of ribs 33*a* and the second set of ribs 33*b* is disposed at an angle with respect to a sidewall of one of the first chamber 6 and the second chamber 7, and the other of the first set of ribs 33*a* and the second set of ribs 33*b* is disposed in a substantially parallel or substantially perpendicular orientation with respect to the sidewall of the other of the first chamber 6 and the second chamber 7. Such distinct rib orientations may provide such a visual indicator 53 evidencing a differentiation between the first chamber 6 and second chamber 7. The precise arrangement of the rib orientation may take various forms and arrangements. Optionally, the visual indicator 53 may also include a removable membrane over one or both of first chamber 6 and second chamber 7. In another embodiment, the visual indicator 53 may include forming the first chamber 6 from a first colored material and forming the second chamber 7 from a different colored material.

Figure 8:
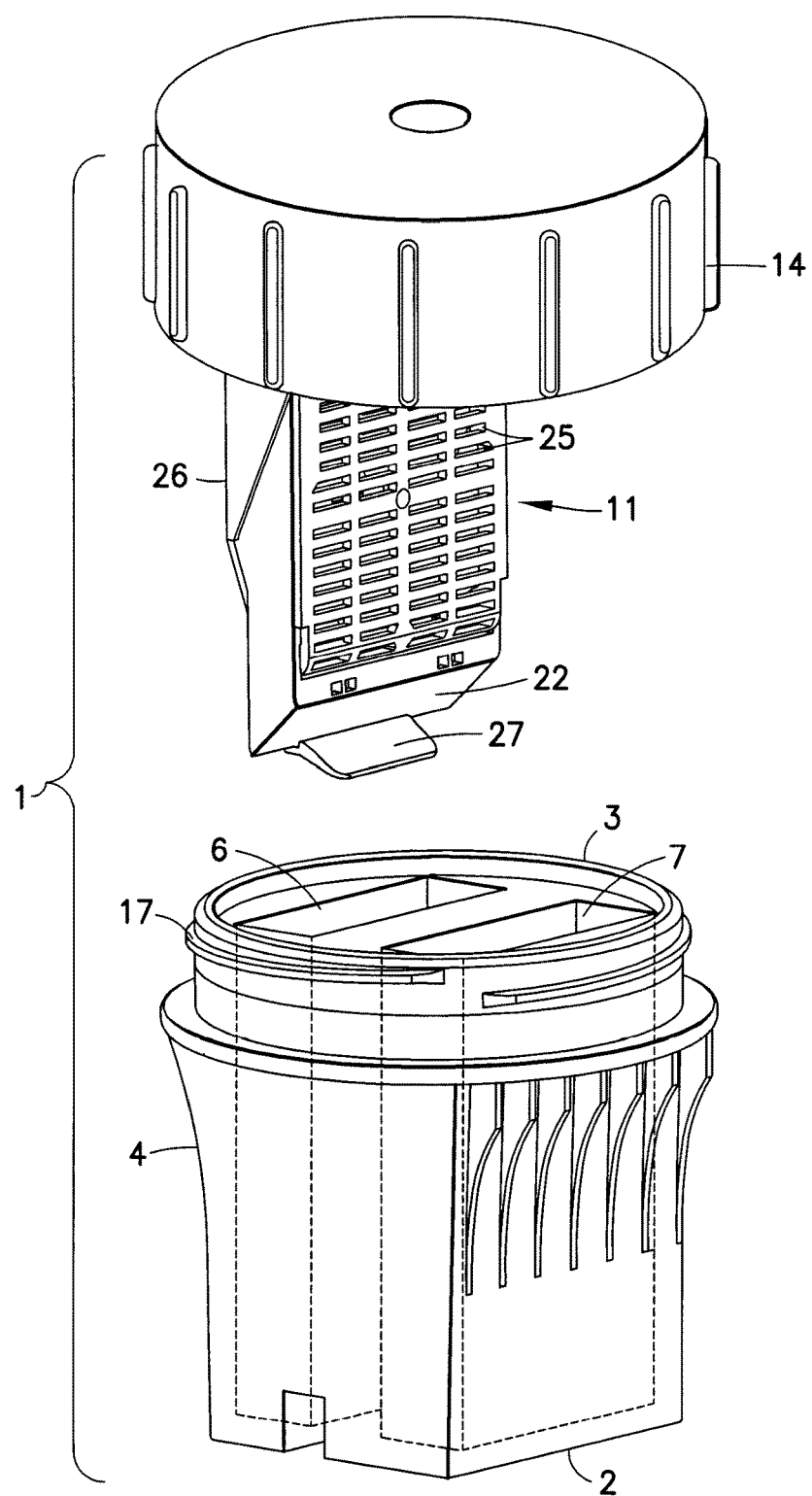
FIG. 8 is a partially exploded perspective view of the container of FIG. 1 shown with the sample holder being inserted into the first chamber.

Referring to FIG. 8, the container 1 may be assembled and provided with liquid, such as solutions or reagents, within first chamber 6 and/or second chamber 7, at the point of manufacture. Alternatively, any such liquid may be filled into the first chamber 6 and/or the second chamber 7 at any point prior to use, such as directly prior to inserting a tissue sample into sample holder 11.

Container 1 may be provided for use with a one reagent system. In this manner, a single reagent solution, such as a tissue fixative like formalin, may be provided within second chamber 7. Such fixative solutions stabilize the RNA within a tissue sample, for conducting molecular diagnostic testing. Alternatively, container 1 may be provided for use with a two solution or a two reagent system. For example, a wash solution may be provided in second chamber 7, so as to dilute the first reagent fixative in the first chamber 6. It is also possible that first chamber 6 and second chamber 7 contains the same reagent since it may be advantageous to transfer a biological sample from a reagent to a fresh amount of the same reagent after a period of time has passed. Or, a first reagent solution, such as a tissue fixative like formalin, may be used within first chamber 6, and a second reagent solution, such as a stabilizer in the form of a nucleic acid stabilization reagent, for stabilizing the morphology of the tissue sample, may be provided within second chamber 7.

Any reagents may be used with the container of the present invention. For example, the fixative may be formalin, ethanol solutions, Carnoy's solution I (ethanol and acetic acid), Carnoy's Solution II (ethanol, chloroform and acetic acid), methacarn (methanol, chloroform and acetic acid), Clark's fixative, Boonfix, and the like. A non-limiting list of commercially available fixatives includes, but is not limited to, MIRSKY'S FIXATIVE (available from National Diagnostics, Inc. of Atlanta, Ga.); GLYOFIX (available from Shandon Lipshaw, Inc. of Pittsburgh, Pa.); HISTOCHOICE (available from Amresco); HISTOFIX (available from Trend Scientific, New Brighton, Minn.); KRYOFIX (available from Merck); MICROFIX (available from Energy Beam Sciences, Inc., East Granbury, Conn.); NEOFIX (available from Merck); NOTOX (available from Earth Safe Industries, Inc., Belle Mead, N.J.); OMNIFIX II and OMNI-FIX 2000 (available from AnCon Genetics, Inc, Mellville, N.Y.); PREFER (available from Anatech Ltd, Battle Creek, Mich.); PRESERVE (available from Energy Beam Sciences, Inc., East Granbury, Conn.); SAFEFIX II (available from Thermo Fischer Scientific, Inc.); STATFIX (available from StatLab Medical Products, Inc. of Lewisville, Tex.); STF (Streck Tissue Fixative, available from Streck Laboratories, Omaha, Neb.); UMFIX (available from Sakura Finetek USA, Inc., Torrance, Calif.); and FINEFIX (available from Milestone Medical of Shelton, Conn.). Commercially available stabilizers include, but are not limited to, RNALATER (available from Ambion, Inc., Austin, Tex.) and RNEASY (available from Qiagen, Inc., Valencia, Calif.). Any other reagents known or hereafter discovered for use as fixatives and/or stabilizers are intended as useful in the present invention.

In one embodiment, the second chamber 7 of container 1 is filled with the desired liquid, and a peel-away cover 30, such as shown in FIG. 9, may be adheredly placed thereover. Thereafter, first chamber 6 may be filled with a different liquid medium (for example, in embodiments involving a two reagent system). Closure 14, with or without sample holder 11 extending therefrom, is then placed over the container top 3 and threadably mated therewith, as shown in FIG. 10. The container 1 thus assembled may be packaged in a separate package, if desired, and stored for use.

Referring again to FIG. 8, in use, a biological sample, such as a tissue sample extracted from a patient for molecular or histology diagnostics testing, is placed within the cavity 24 (shown in FIG. 4A) within sample holder 11. In embodiments where sample holder 11 is provided as a separate element, closure 14 can be removed from container 1 and sample holder 11 may then be inserted into the receiving member 26 of closure 14. Alternatively, if sample holder 11 is provided with closure 14, the tissue sample may be placed within sample holder 11 after closure 14 is removed from the container 1, either with sample holder 11 connected thereto, or by removing sample holder 11 therefrom and then reattaching it thereto.

Closure 14 with sample holder 11 containing the tissue sample therein is thereafter placed over the container top 3, with sample holder 11 aligned within and placed into first chamber 6, as shown in FIG. 8. Closure 14 is then mated with container 1, such as by rotating closure 14 and/or the container housing with respect to each other in a threaded engagement. During such respective rotation, sample holder 11 can maintain its orientation within first chamber 6, since first chamber 6 is sized and oriented for accommodating the particular shape of sample holder 11. As closure 14 is torqued down onto container 1, seal surface 15 engages surface 12 of container 1, providing a fluid tight seal.

Figure 7:
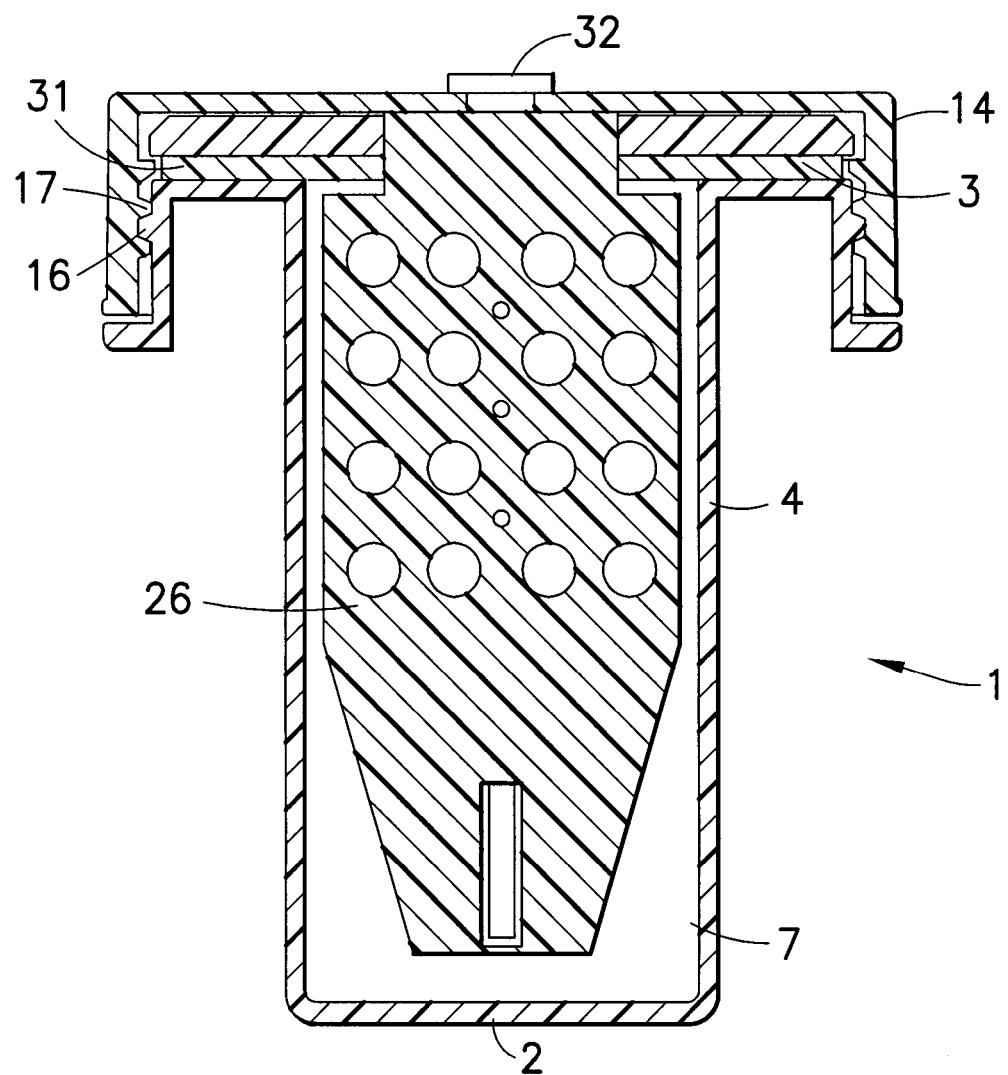
FIG. 7 is a cross-sectional view of the container taken along line 7-7 of FIG. 1, shown without the sample holder therein.

In embodiments including a one reagent system as discussed above, the tissue sample is at this point contained within sample holder 11 in first chamber 6 in isolation from the reagent within second chamber 7. When it is desired to contact the tissue sample with the reagent, the user removes closure 14 from the container 1, thereby removing sample holder 11 from first chamber 6. Peel-away cover 30, such as a foil or label, if used, can then be removed, exposing second chamber 7, and the sample holder 11 can then be inserted into second chamber 7, as shown in FIG. 7. With sample holder 11 attached to closure 14 of container 1 the sample holder 11 can be transferred from first chamber 6 into second chamber 7, without the user coming into direct contact with sample holder 11 after it is attached to closure 14, thus avoiding potential contamination of the biological sample. Moreover, by maintaining the tissue sample in fluid isolation from the fluid or reagent contained within the second chamber 7, contact between the sample and the fluid can be precisely regulated until a desired time. Furthermore, the length of time the tissue sample contacts the fluid or reagent can be precisely regulated and monitored.

Referring again to FIG. 8, in embodiments including a two reagent system as discussed above, when the sample holder 11 is placed within first chamber 6, the tissue sample is placed in contact with the first reagent contained within first chamber 6, with such reagent flowing through the fluid openings 25 of sample holder 11, thereby contacting the tissue sample contained within the internal cavity 24 (shown in FIG. 4A) thereof. The tissue sample can be maintained in contact with the fluid or reagent within the first chamber 6 for a specified time period, after which time the closure 14 can be removed and repositioned such that sample holder 11 is placed into second chamber 7, as discussed above with reference to FIG. 7. Thus, the second fluid or reagent maintained within second chamber 7 can contact the tissue sample contained within the sample holder 11. After contact with the second fluid or reagent for a desired time period, the closure 14 may be removed so as to remove the tissue sample from sample holder 11 for any desired diagnostic testing.

Since sample holder 11 is connected with closure 14, access to the tissue sample contained within sample holder 11 can be achieved by removing closure 14 from container 1 and inverting it, placing the outer surface on a counter, thereby preventing sample holder 11 from being exposed. Any fluid that is contained within sample holder 11 can drip downward within the bottom or internal surface of closure 14 and be caught by the rim surrounding closure 14, thereby preventing any leakage or spillage onto the counter surface. The sample holder 11 may be openable while the sample holder 11 is connected with the closure 14, thereby providing a simple access to the tissue sample contained therein, and providing a proper support for maintaining the sample holder 11 in place without having to physically contact any portion of the sample holder to hold it in place while accessing the sample, thereby preventing any potential for contamination of the sample based on contact by the user. Thereafter, the container 1 may be washed and re-used, or more preferably, will be discarded to prevent cross-contamination with other samples.

Figure 13:
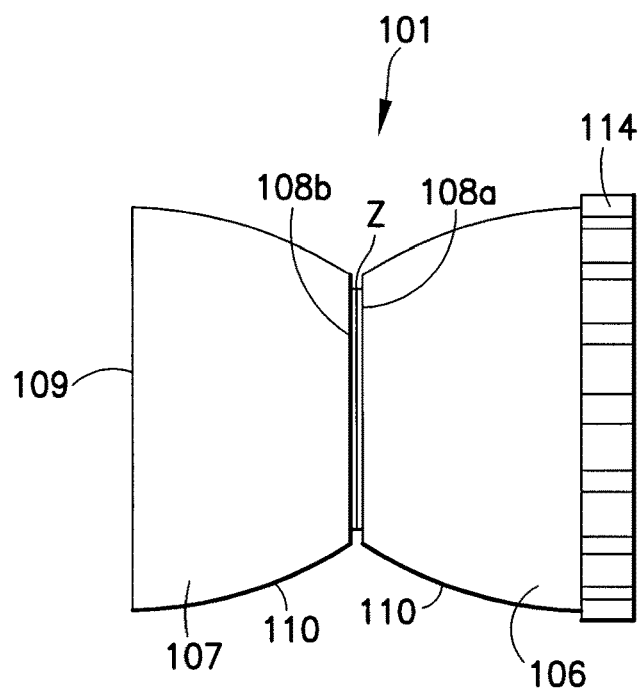
FIG. 13 is a front view of a container in accordance with a further embodiment of the present invention, in which the bottom end of a first chamber is integrated with the bottom end of a second chamber.

Referring now to FIG. 13, an alternative embodiment of container is shown. In this embodiment, container 101 includes a first chamber 106 and a second chamber 107, in which each chamber has an open top end 109, a closed bottom end 108a-b, and a sidewall 110 extending between the open end 109 and the closed end 108a-b. The first chamber 106 and second chamber 107 are arranged so that the bottom end of the first chamber 108a is directly adjacent, or abuts, the bottom end of the second chamber 108b. In this arrangement, bottom end of the first chamber 108a conjoins with bottom end of the second container 108b along a common plane Z. Bottom end of the first chamber 108a is in this way integrated with bottom end of the second chamber 108b. First chamber 106 and second chamber 107 are dimensioned so that the same sample holder 11 can be disposed therein. Coupled to first chamber 106 is closure 114 for enclosing the open end 109. Closure 114 is capable of engaging the open end 109 of first chamber 106 and second chamber 107 mutually exclusively. Closure 114 in this embodiment is consistent with closure 14 disclosed above in connection with other embodiments.

Figure 14:
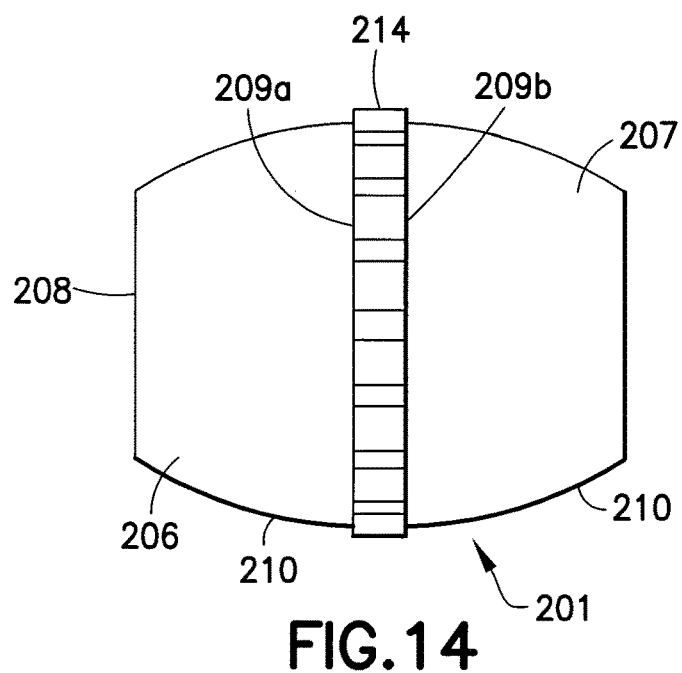
FIG. 14 is a front view of a container in accordance with a further embodiment of the present invention, in which a closure is disposed between the open end of a first chamber and the open end of a second chamber.
Figure 15B:
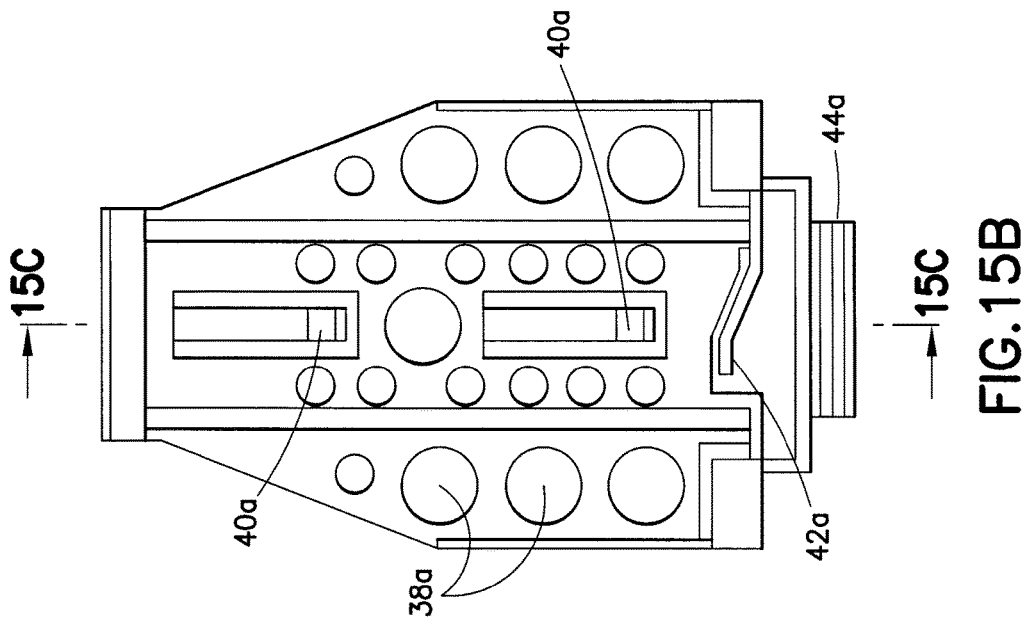
FIG. 15B is a front view of the receiving element of FIG. 15A.
Figure 15A:
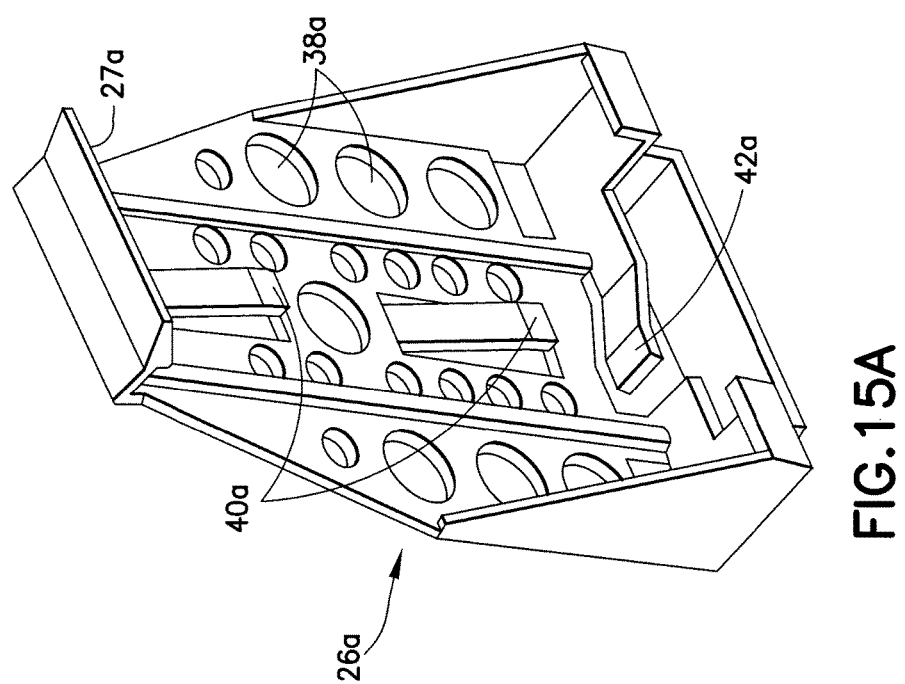
FIG. 15A is a perspective view of an embodiment of a receiving element for use in connection with the present invention.
Figures 15C, 15D:
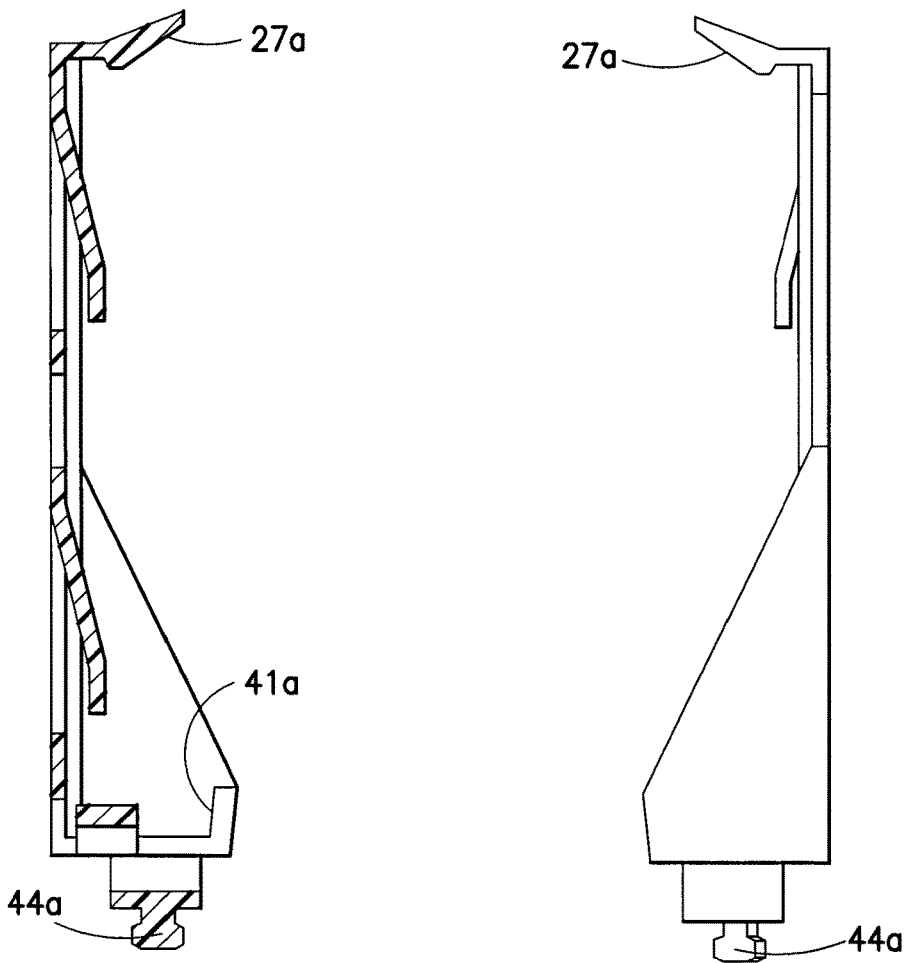
FIG. 15C is a side sectional view of the receiving element taken along line 15C-15C of FIG. 15B.
FIG. 15D is a side view of the receiving element of FIG. 15A.
Figure 15E:
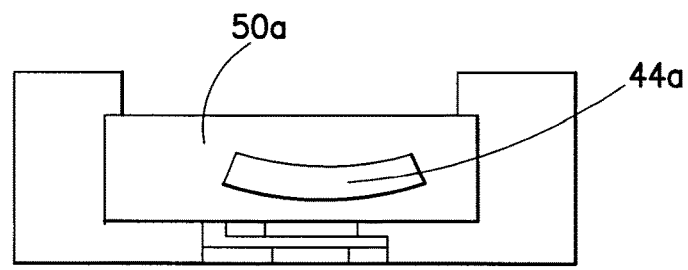
FIG. 15E is a top view of the receiving element of FIG. 15A.

Referring now to FIG. 14, another alternative embodiment of container is shown. In this embodiment, container 201 includes a first chamber 206 and a second chamber 207, where each chamber has an open top end 209a-b, a closed bottom end 208, and a sidewall 210 extending between the open end 209a-b and the closed end 208. First chamber 206 and second chamber 207 are dimensioned so that the same sample holder 11 can be disposed therein. First chamber 206 and second chamber 207 are arranged so that a closure 214 is disposed between first chamber 206 and second chamber 207. Closure 214 is matable with first chamber 206 at open top end 209a and with second chamber 207 at open top end 209b in any manner, such as a frictional fit, snap fit, threadable engagement, interlocking structural engagement, or other manner, providing a liquid tight seal.

While embodiments of the present invention are satisfied in many different forms, there is shown in the figures and described herein in detail, specific embodiments of the invention, with the understanding that the present disclosure is to be considered as exemplary of the principles of the invention and is not intended to limit the invention to the embodiments illustrated. Various other embodiments will be apparent to, and readily made by those skilled in the art, without departing from the scope and spirit of the invention. For example, while two chambers have been described herein, it is contemplated that the container described herein can include any number of chambers for containing varying reagents therein. The scope of the invention will be measured by the appended claims and their equivalents.

What is claimed is:

1. A sample holder receiving member, comprising:
a generally planar frame comprising:
a plurality of surfaces configured to confine a tapered end of a sample holder within the generally planar frame and engage at least opposing ends of the sample holder; and
at least one cantilevered finger extending from the frame, the cantilevered finger being deflectable from a less stressed state to a more stressed state when the sample holder is engaged within the plurality of surfaces, thereby maintaining the sample holder within the frame of the receiving member; and
a platform extending substantially perpendicular to a plane encompassed by the generally planar frame, wherein the platform is pivotably connectable to a closure for a specimen collection container such that the platform is rotatable with respect to the closure, and wherein the platform is fully encompassed by the closure and the specimen collection container when the closure is mated to the specimen collection container.

2. The sample holder receiving member of claim 1, wherein at least one of the plurality of surfaces is a confining latch, the confining latch being deflectable to accommodate an edge of the sample holder.

3. The sample holder receiving member of claim 2, wherein the confining latch is configured to engage a tapered end of the sample holder, thereby holding the sample holder in place against at least one of the plurality of surfaces of the frame.

4. The sample holder receiving member of claim 1, comprising a plurality of cantilevered fingers extending from the frame.

* * * * *